(12) United States Patent
Wasielewski et al.

(10) Patent No.: US 8,956,418 B2
(45) Date of Patent: Feb. 17, 2015

(54) SMART JOINT IMPLANT SENSORS

(75) Inventors: Ray C. Wasielewski, New Albany, OH (US); Richard D. Komistek, Knoxville, TN (US); Mohamed R. Mahfouz, Knoxville, TN (US)

(73) Assignee: Zimmer, Inc., Warsaw (IN)

(*) Notice: Subject to any disclaimer, the term of this patent is extended or adjusted under 35 U.S.C. 154(b) by 1270 days.

(21) Appl. No.: 11/890,307

(22) Filed: Aug. 3, 2007

(65) Prior Publication Data

US 2008/0065225 A1 Mar. 13, 2008

Related U.S. Application Data

(63) Continuation of application No. PCT/US2006/005545, filed on Feb. 18, 2006.

(60) Provisional application No. 60/654,650, filed on Feb. 18, 2005.

(51) Int. Cl.
A61F 2/30 (2006.01)
A61B 5/00 (2006.01)
A61F 2/38 (2006.01)
(Continued)

(52) U.S. Cl.
CPC ..... A61B 5/4528 (2013.01); *A61F 2002/30878* (2013.01); *A61F 2002/30133* (2013.01); *A61B 5/14532* (2013.01); *A61F 2002/4632* (2013.01); A61F 2/38 (2013.01); A61F 2/4684 (2013.01); G06F 19/327 (2013.01); *A61B 2562/028* (2013.01); *A61F 2/3859* (2013.01); *A61F 2230/0015* (2013.01); *A61F 2002/30673* (2013.01); *A61F 2/4657* (2013.01); *A61F 2002/488* (2013.01); G06F 19/3418 (2013.01); *A61B 5/145* (2013.01); *A61F 2002/4666* (2013.01); A61L 27/50 (2013.01); *A61F 2/389* (2013.01); *A61F 2002/3067* (2013.01);
(Continued)

(58) Field of Classification Search
USPC ................................................ 623/914, 18.11
See application file for complete search history.

(56) References Cited

U.S. PATENT DOCUMENTS 3,915,015 A 10/1975 Crane et al.
4,501,266 A 2/1985 McDaniel
(Continued)

FOREIGN PATENT DOCUMENTS

DE 4017646 A1 12/1991
WO WO03/002022 A2 1/2003
(Continued)

OTHER PUBLICATIONS

T.K. Fehring, et al, "Early Failures in Total Knee Orthoplasty," Clin Orthop, 2001, pp. 315-318, vol. 382.
(Continued)

*Primary Examiner* — Bruce E Snow
*Assistant Examiner* — Melissa Hoban

(57) ABSTRACT

A prosthesis for implantation into a mammalian body, the device comprising: (a) a prosthesis for implantation into a mammalian body that includes a sensor array comprising a plurality of sensors mounted to the prosthesis; and (b) an electronics structure for receiving signals from the sensor array and wirelessly transmitting representative signals to a remote receiver, where the plurality of sensors are operative to sense pressure, applied to the prosthesis by another object, in at least two axes generally perpendicular to one another.

29 Claims, 17 Drawing Sheets

(51) Int. Cl.
*G06F 19/00* (2011.01)
*A61L 27/50* (2006.01)
*A61B 5/03* (2006.01)
*A61B 5/07* (2006.01)
*A61B 5/145* (2006.01)
*A61F 2/46* (2006.01)
*A61F 2/48* (2006.01)

(52) U.S. Cl.
CPC . *A61B5/03* (2013.01); *A61B 5/076* (2013.01); *A61B 5/14539* (2013.01); *A61F 2250/0002* (2013.01)
USPC .................. 623/18.11; 600/309; 623/20.14

(56) References Cited

U.S. PATENT DOCUMENTS

| | | |
|---|---|---|
| 4,503,705 A | 3/1985 | Polchaninoff |
| 4,822,362 A | 4/1989 | Walker et al. |
| 4,997,445 A | 3/1991 | Hodorek |
| 5,085,252 A | 2/1992 | Mohamed et al. |
| 5,197,488 A | 3/1993 | Kovacevic |
| 5,326,363 A | 7/1994 | Aikins |
| 5,360,016 A | 11/1994 | Kovacevic |
| 5,412,619 A | 5/1995 | Bauer |
| 5,425,775 A | 6/1995 | Kovacevic et al. |
| 5,456,724 A | 10/1995 | Yen et al. |
| 5,465,760 A | 11/1995 | Mohamed et al. |
| 5,470,354 A | 11/1995 | Hershberger et al. |
| 5,518,008 A | 5/1996 | Cucchiaro et al. |
| 5,529,070 A | 6/1996 | Augustine et al. |
| 5,645,077 A | 7/1997 | Foxlin |
| 5,656,785 A | 8/1997 | Trainor et al. |
| 5,669,914 A | 9/1997 | Eckhoff |
| 5,678,448 A | 10/1997 | Fullen et al. |
| 5,719,324 A | 2/1998 | Thundat et al. |
| 5,733,292 A | 3/1998 | Gustilo et al. |
| 5,777,467 A | 7/1998 | Arms et al. |
| 5,807,284 A | 9/1998 | Foxlin |
| 5,840,047 A | 11/1998 | Stedham |
| 5,876,325 A | 3/1999 | Mizuno et al. |
| 5,879,398 A | 3/1999 | Swarts et al. |
| 5,941,904 A | 8/1999 | Johnston et al. |
| 6,034,296 A | 3/2000 | Elvin et al. |
| 6,073,484 A * | 6/2000 | Miller et al. ................. 73/105 |
| 6,122,538 A | 9/2000 | Sliwa, Jr. et al. |
| 6,122,541 A | 9/2000 | Cosman et al. |
| 6,129,122 A | 10/2000 | Bilisik |
| 6,143,035 A | 11/2000 | McDowell |
| 6,162,191 A | 12/2000 | Foxlin |
| 6,165,135 A | 12/2000 | Neff |
| 6,216,537 B1 | 4/2001 | Henschel et al. |
| 6,245,109 B1 | 6/2001 | Mendes et al. |
| 6,281,149 B1 | 8/2001 | Hussein et al. |
| 6,283,168 B1 | 9/2001 | Gu et al. |
| 6,285,902 B1 | 9/2001 | Kienzle et al. |
| 6,307,481 B1 | 10/2001 | Lehrman et al. |
| 6,312,393 B1 * | 11/2001 | Abreu ........................ 600/558 |
| 6,315,007 B1 | 11/2001 | Mohamed et al. |
| 6,345,598 B1 | 2/2002 | Bogdanovich et al. |
| 6,361,507 B1 | 3/2002 | Foxlin |
| 6,425,923 B1 | 7/2002 | Stalcup et al. |
| 6,439,096 B1 | 8/2002 | Mungalov et al. |
| 6,447,448 B1 | 9/2002 | Ishikawa et al. |
| 6,447,886 B1 | 9/2002 | Mohamed et al. |
| 6,474,159 B1 | 11/2002 | Foxlin et al. |
| 6,513,381 B2 | 2/2003 | Fyfe et al. |
| 6,523,392 B2 | 2/2003 | Porter et al. |
| 6,553,681 B2 | 4/2003 | Ekholm et al. |
| 6,567,703 B1 | 5/2003 | Thompson et al. |
| 6,573,706 B2 | 6/2003 | Mendes et al. |
| 6,583,630 B2 | 6/2003 | Mendes et al. |
| 6,610,096 B2 | 8/2003 | MacDonald |
| 6,611,141 B1 | 8/2003 | Shulz et al. |
| 6,661,347 B2 | 12/2003 | Lehrman et al. |
| 6,706,005 B2 | 3/2004 | Roy et al. |
| 6,733,533 B1 | 5/2004 | Lozier |
| 6,786,877 B2 | 9/2004 | Foxlin |
| 6,820,025 B2 | 11/2004 | Bachmann et al. |
| 6,909,985 B2 | 6/2005 | Stana |
| 6,950,025 B1 | 9/2005 | Nguyen |
| 7,000,469 B2 | 2/2006 | Foxlin et al. |
| 7,028,547 B2 | 4/2006 | Shiratori et al. |
| 7,097,662 B2 | 8/2006 | Evans, III et al. |
| 7,104,130 B2 | 9/2006 | Kenny et al. |
| 7,180,409 B2 | 2/2007 | Brey |
| 7,195,645 B2 | 3/2007 | Disilvestro et al. |
| 7,204,145 B2 | 4/2007 | Heinks et al. |
| 7,325,453 B2 | 2/2008 | Bremer et al. |
| 7,575,602 B2 | 8/2009 | Amirouche et al. |
| 7,591,854 B2 | 9/2009 | Wasielewski |
| 7,632,283 B2 | 12/2009 | Heldreth |
| 2001/0012932 A1 | 8/2001 | Peer |
| 2002/0102743 A1 | 8/2002 | Majumdar et al. |
| 2002/0104376 A1 | 8/2002 | Danyluk et al. |
| 2002/0130673 A1 | 9/2002 | Pelrine et al. |
| 2002/0180306 A1 | 12/2002 | Hunt et al. |
| 2003/0003135 A1 | 1/2003 | Leung et al. |
| 2003/0026758 A1 | 2/2003 | Baker |
| 2003/0069591 A1 | 4/2003 | Carson et al. |
| 2003/0069644 A1 | 4/2003 | Kovacevic et al. |
| 2003/0114735 A1 * | 6/2003 | Silver et al. ................... 600/300 |
| 2003/0119398 A1 | 6/2003 | Bogdanovich et al. |
| 2004/0019384 A1 | 1/2004 | Kirking et al. |
| 2004/0064191 A1 | 4/2004 | Wasielewski |
| 2004/0080319 A1 | 4/2004 | Merrill |
| 2004/0097952 A1 | 5/2004 | Sarin et al. |
| 2004/0152970 A1 | 8/2004 | Hunter et al. |
| 2004/0243148 A1 | 12/2004 | Sasielewski |
| 2005/0010302 A1 | 1/2005 | Dietz et al. |
| 2005/0068044 A1 | 3/2005 | Peine et al. |
| 2005/0116673 A1 | 6/2005 | Carl et al. |
| 2005/0131390 A1 | 6/2005 | Heinrich et al. |
| 2005/0146076 A1 | 7/2005 | Alexander et al. |
| 2005/0165317 A1 | 7/2005 | Turner et al. |
| 2005/0171456 A1 * | 8/2005 | Hirschman et al. ........... 600/592 |
| 2005/0186081 A1 | 8/2005 | Mohamed |
| 2005/0234555 A1 * | 10/2005 | Sutton et al. ................ 623/17.15 |
| 2005/0245820 A1 | 11/2005 | Sarin |
| 2005/0273170 A1 | 12/2005 | Navarro et al. |
| 2006/0004431 A1 | 1/2006 | Fuller et al. |
| 2006/0047283 A1 | 3/2006 | Evans et al. |
| 2006/0058604 A1 | 3/2006 | Avinash et al. |
| 2006/0075816 A1 | 4/2006 | Bremer et al. |
| 2006/0142657 A1 | 6/2006 | Quaid et al. |
| 2006/0150734 A1 | 7/2006 | Mimnaugh-Kelleher et al. |
| 2006/0235314 A1 | 10/2006 | Migliuolo et al. |
| 2006/0254369 A1 | 11/2006 | Yoon et al. |
| 2006/0271199 A1 | 11/2006 | Johnson |
| 2006/0282168 A1 * | 12/2006 | Sherman et al. ........... 623/18.12 |
| 2007/0032748 A1 | 2/2007 | McNeil et al. |
| 2007/0065077 A1 | 3/2007 | Childers et al. |
| 2007/0189902 A1 | 8/2007 | Mohamed |
| 2007/0219641 A1 | 9/2007 | Dorr et al. |
| 2007/0225731 A1 | 9/2007 | Couture et al. |
| 2007/0233258 A1 | 10/2007 | Hestad et al. |
| 2007/0270686 A1 | 11/2007 | Ritter et al. |
| 2007/0287911 A1 | 12/2007 | Haid et al. |
| 2008/0010705 A1 | 1/2008 | Quaid et al. |
| 2008/0010706 A1 | 1/2008 | Moses et al. |
| 2008/0039868 A1 | 2/2008 | Tuemmler et al. |
| 2008/0064947 A1 | 3/2008 | Heruth et al. |
| 2008/0081982 A1 | 4/2008 | Simon et al. |
| 2008/0097187 A1 | 4/2008 | Geilen et al. |
| 2008/0123921 A1 | 5/2008 | Geilen et al. |
| 2008/0130965 A1 | 6/2008 | Avinash et al. |

FOREIGN PATENT DOCUMENTS

| | | |
|---|---|---|
| WO | WO03/026518 A1 | 4/2003 |
| WO | WO03/071969 A1 | 9/2003 |
| WO | WO03/077775 A1 | 9/2003 |

(56) References Cited

FOREIGN PATENT DOCUMENTS

| WO | PCT/US06/05545 | 6/2007 |
|---|---|---|
| WO | PCT/US06/05545 | 8/2007 |
| WO | WO2007/136784 A2 | 11/2007 |

OTHER PUBLICATIONS

J.F. Brick, et al, "The Patellofemoral Component of Total Knee Arthroplasty," Clin Orthop, 1988, pp. 163-178, vol. 231.

G. Bergmann, et al, "Hip Joint Loading During Walking and Running Measured in Two Patients," J of Biomechanics, 1993, pp. 969-990, vol. 26, Issue 8.

G. Bergmann, et al, "Frictional Heating of Total Hip Implants, Part I Measurements in Patients," J of Biomechanics, 2001, pp. 421-428, vol. 34.

G.M. Kotzar, et al, "Telemeterized in Vivo Hip Joint Force Data: A Report on Two Patients After Total Hip Surgery," J of Ortho Research, 1989, pp. 621-633, vol. 9, Issue 5.

D.T. Davy, et al, "Telemetric Force Measurements Across the Hip after Total Arthroplasty," J of Bone and Joint Surgery, 1998, pp. 45-50, vol. 70-A, Issue 1.

K.R. Kaufman, et al, "Instrumented Implant for Measuring Tibiofemoral Forces," J of Biomechanics, 1996, pp. 667-671, vol. 29, Issue 5.

S.J.G. Taylor, et al, "Forces and Moments Telemetered from two Distal Femoral Replacement During Various Activities," J of Biomech, 2001, pp. 829-848, vol. 34.

P.F. Sharkey, et al, "Why are Total Knee Anthroplasties Failing Today?," Clin Orthop, 2002, pp. 7-13, vol. 404.

Cooper et al., James A. Fiber-Based Tissue-Engineered Scaffold for Ligament Replacement: Design Considerations and In Vitro Evaluation, Biomaterials 26 (2005) 1523-1532, Elsevier Ltd. @ www.elsevier.com/locate/biomaterials (Cooper).

Shenfang, Yuan, Determination of Internal Strain in 3-D Braided Composites Using Optic Fiber Strain Sensors, Acta Mechanica Solida Sinica, vol. 17, No. 1, Mar. 2004, HUST, Wuhan, China (Shenfang).

Wang, Zhong Lin and Jinhui Song, Piezoelectric Nanogenerators Based on Zinc Oxide Nanowire Arrays, Science, vol. 312, Apr. 14, 2006 at www.sciencemag.org. (Wang).

Science@NASA, The Right Stuff for Super Spaceships from http://science.nasa.gov/headlines/y2002/16sep_rightstuff.htm7/2/2008 (Science).

* cited by examiner $$u_{EOF} = \frac{\varepsilon \zeta}{4\pi\eta} E$$

Electroosmotic flow — dielectric constant, zeta potential, Flow velocity, viscosity $$V = \frac{\sigma_w L_D}{\eta} E$$

Charge density, Debye Length

SMART JOINT IMPLANT SENSORS

CROSS REFERENCE TO RELATED APPLICATIONS

This application is a continuation that claims priority under 35 U.S.C. §120 of Patent Cooperation Treaty Application Serial No. PCT/US2006/005545 filed on Feb. 18, 2006, entitled "SMART JOINT IMPLANT INSERTS," which claimed priority under 35 U.S.C. §119 to U.S. Provisional Patent Application Ser. No. 60/654,650, filed Feb. 18, 2005, entitled "SURGICAL SMART INSERTS," the disclosure of which is hereby incorporated by reference.

RELATED ART

1. Field of the Invention

The present invention is directed to sensors for utilization in the health care industry and, more specifically, to miniature sensors for use in prosthetic implants and prosthetic trials.

2. Prospective of Related Art

Failure of total joint arthroplasty (TJA) can be a rapid or insidious process. In cases of rapid failure, the diagnosis is often obvious, but unfortunately often too late to avoid surgical revision. Fortunately, most joint replacements simulate the joints of the body and slowly degrade over time for more subtle mechanical and biologic reasons. If a reliable detection method or system was operative to detect insidious or subtle failure and infection, these conditions can be mitigated or even reversed.

TJA failure etiologies can be divided generally into mechanical and biologic causes. The mechanical causes are generally wear of the articular surfaces and loosening of the prosthetic components. Abnormal loading conditions that are present immediately post-operatively or that worsen over time can directly affect the wear process. By the time these processes are apparent using conventional detection methods (e.g., linear wear on radiographs, implant-bone junction radiolucencies, and osteolytic bone defects from excessive particulate wear debris) it is often too late for optimum implant survival to be achieved. By the time lucencies are seen between the various components and the bone, loosing has occurred and failure is eminent. Only early detection of these impending failures can allow for the possibility for simple or more conservative interventions to correct joint mechanical anomalies before becoming irreversible.

Biologic failure of the TJA can be attributable to inflammation or infection. Aseptic loosening can be seen as progressive radiolucencies on radiographs, but once again, too late for effective intervention. However, subtle changes in the synovial fluid might signal an insidious failure, thereby allowing non-operative intervention as opposed to complete revision surgery.

The markers for different failure modes of prosthetic implants are known. The following listing of references is indicative of the current knowledge regarding these markers. For example, increased pressure associated with the synovial fluid may be indicative of infection (see http://www.k-com.edu/faculty/chamberlain/Website/lectures/tritzid/septarthritis.htm (septic arthritis)). In addition, is has been observed that synovial fluid having a low pH may be indicative of infection (see http://www.kcom.edu/faculty/chamberlain/Website/lectures/tritzid/septarthritis.htm (septic arthritis)) (see also Tulamo R. M. et al., Equine Vet. J., 1989 September; 21(5):325-31 (infectious arthritis, horse for pH below 6.9). The following references also acknowledge other markers indicative of infections: (1A) leukocyte (WBC) count is increased (see Trampuz A. et al., Am. J. Med., 2004 Oct. 15; 117(8):556-62 (infected TKA); (1B) leukocyte (WBC) count is greater than or equal to 2500 per milliliter (see Mason J. B. et al., J. Arthroplasty, 2003 December; 18(8):1038-43 (revision TKA)); (2A) neutrophil (polymorphonuclear cells (PMNCs)) percentage is increased (see Trampuz A. et al., Am. J. Med., 2004 Oct. 15; 117(8):556-62 (infected TKA)); (2B) neutrophil (polymorphonuclear cells (PMNCs)) percentage is greater than or equal to 60% (see Mason J. B. et al., J. Arthroplasty, 2003 December; 18(8):1038-43 (revision TKA)); (3) presence of bacterial deoxyribonucleic acid (detected by polymerase chain reaction) (see Mariani B. D. et al., Clin. Orthop., 1996 October; (331):11-22).

Additional markers associated with synovial fluid that are indicative of infection include: (4) presence of antibodies (see http://www.kcom.edu/faculty/chamberlain/Website/lectures/tritzid/septarthritis.htm (septic arthritis)); (5A) low glucose concentration (must compare to blood glucose level) (see Tulamo R. M. et al., Equine Vet. J., 1989 September; 21(5):325-31 (infectious arthritis, horse)); (5B) low glucose concentration of less than 40 mg/dL (see http://my.webmd.com/hw/arthritis/hw231503.asp); (5C) low glucose concentration less than 0.6% (see http://www.kcom.edu/faculty/chamberlain/Website/lectures/tritzid/septarthritis.htm (septic arthritis); (6A) elevated protein level (see Tulamo R. M. et al., Equine Vet. J., 1989 September; 21(5):325-31 (infectious arthritis, horse)); (6B) elevated protein level greater than or equal to 3 g/dL (see http://my.webmd.com/hw/arthritis/hw231503.asp); (7) higher concentration of excitatory amino acids (EAA) glutamate and aspartate (also related to arthritis) (see McNeamey T. et al., J. Rheumatol., 2000 March; 27(3):739-45); (8a) elevated level of lactate dehydrogenase (when blood levels of LDH are normal) (see Tulamo R. M. et al., Equine Vet. J., 1989 September; 21(5):325-31. (infectious arthritis, horse); (8b) elevated level of lactate dehydrogenase (when blood levels of LDH are normal) greater than 333 IU/L (see http://my.webmd.com/hw/arthritis/hw231503.asp); and (9) white cell gene expression (see Deirmengian C., Clin. Orthop. Related Res., November 2005; 440:38-40).

Those of ordinary skill are familiar with other markers such as, without limitation, lower viscosity of the synovial fluid (see Mazzucco D. et al., J. Orthop. Res., 2002 November; 20(6): 1157-63) and lower hyaluronic acid (HA) content (see Mazzucco D. et al., Biomaterials, 2004 August; 25(18):4433-45) signifying a failing or failed TKA. Other markers, such as, without limitation, the presence of uric acid crystals (monosodium urate monohydrate crystals) (see Ryckman C. et al., Arthritis Rheum., 2003 August; 48(8):2310-20), the presence of calcium pyrophosphate crystals indicates pseudogout (see http://my.webmd.com/hw/arthritis/hw231503.asp), elevated leukocyte count (see Canoso J. J. et al., Arthritis Rheum., 1979 December; 22(12):1361-4), elevated level of lactate dehydrogenase (when blood levels of LDH are normal) greater than 333 IU/L (see http://my.webmd.com/hw/arthritis/hw231503.asp), elevated MMP-9 (gelatinase-B) antigen levels (see Hsieh M. S. et al., J. Cell. Biochem., 2003 Jul. 1; 89(4):791-0), and high concentrations of S100A8/A9 (see Ryckman C. et al., Arthritis Rheum., 2003 August; 48(8):2310-20) may be indicative of gout.

Further markers of synovial fluid indicative of arthritic patients include, without limitation, (1) lower concentration, elasticity and viscosity (see Fukuda K., Clin. Calcium, 2004 July; 14(7):103-7. (elasticity and viscosity); Mazzucco D. et al., J. Orthop. Res., 2002 November; 20(6): 1157-63; Moskowitz R. W. et al., Am. J. Orthop., 2004 February; 33(2

Suppl):5-9; Adams M. E. et al., Drug Saf., 2000 August; 23(2):115-30 (Hyaluronan smaller in size (OA)); Adams M. E. et al., Drug Saf., 2000 August; 23(2): 115-30 (Lower concentration of hyaluronan)); (2) higher cell count (see Fawthrop F. et al., Br. J. Rheumatol., 1985 February; 24(1):61-9; Dieppe P. A. et al., Arthritis Rheum., 1988 July; 31(7):882-90); (3) the presence of C reactive protein (CRP) (see Rowe I. F. et al., Ann. Rheum. Dis., 1987 October; 46(10):721-6); (4) higher concentration of amino acids (see McNearney T. et al., J. Rheumatol., 2000 March; 27(3):739-45); (5) higher concentration of excitatory amino acids (EAA) glutamate and aspartate (McNeamey T. et al., J. Rheumatol., 2000 March; 27(3):739-45); (6) presence of rheumatoid factor (RA) (see Sari L. et al., Rev. Med. Chil., 1993 December; 121(12): 1374-81) (7) elevated IgE rheumatoid factor activity (RA) (see Gruber et al., Clin. Exp. Immunol., 1988 February; 71(2):289-94); (8) higher beta-glucuronidase content (OA) (see Fawthrop F. et al., Br. J. Rheumatol., 1985 February; 24(1):61-9); (9) increased nerve growth factor (NGF) concentration (see Halliday D. A. et al., Neurochem. Res., 1998 June; 23(6):919-22); (10) higher levels of insulin-like growth factor I (IGF-I) and its binding proteins (IGFBP) 3 and 4 (in inflammatory joints) (see Kanety H. et al., J. Rheumatol., 1996 May; 23(5):815-8); (11) higher Caeruloplasmin (Cp) concentration (RA and psoriatic arthritis) (see Dixon J. S. et al., Rheumatol Int., 1988; 8(1):11-4); (12) elevated oxidase activity (RA and psoriatic arthritis) (see Dixon J. S. et al., Rheumatol Int., 1988; 8(1): 11-4); and, (13) presence of polyamine oxidases (PAO) (RA) (see Ferrante A. et al., Clin. Exp. Immunol., 1990 June; 80(3):373-5).

Some methods do exist for the detection of failing implants, but often are too late to positively impact treatment. Synovial fluid can be withdrawn from the joint at yearly follow-up, but with an increased risk of causing infection. Labs can be taken each year, but these labs show systemic effects that often occur only after extensive joint damage, where the systemic effects may not necessarily be specific to the joint.

Thus, there is a need in the art for a non-invasive system and associated method to test for these markers in-vivo with the ability to transmit the test/detection data externally to an electronic data storage device during physician follow-ups signals to the patient that the conditions are abnormal, such as a prosthesis vibrating or otherwise objectively signaling to the patient.

INTRODUCTION TO THE INVENTION

The present invention is directed to sensors for utilization in the health care industry and, more specifically, to miniature sensors for use in prosthetic implants and prosthetic trials. The present invention encompasses intelligent implants incorporating sensors operative to measure different mechanical and biologic markers for prosthetic failure. Additionally, the sensors of the present invention are operative to monitor the distributed forces at such joints as the femorotibial and patellofemoral joints, providing a comparison with both post-op and the established norms. A properly balanced knee is neither too loose, nor too tight, and will be reflected from the output from the sensors in the medial and lateral compartments transmitting signals indicative of appropriate joint pressure.

The invention may include a series of microsensing elements ("array") and a micropump fabricated using semiconductor or MEMS (microelectromechanical systems) fabrication technology. The sensors may be arranged in an array of sensing elements that are externally powered by either electromagnetic induction or radio frequency (RF) induction or internally powered using a battery or other power storage device. Data representative of that generated by the sensors is remotely transmitted using RF technology or other alternate technology known to those of ordinary skill or arising hereafter, thereby obviating any reliance on continuous wire-based communication from the sensors to the eventual output device. Pressure sensing elements, temperature sensing elements, and chemical sensing elements may be included in each sensor array in order to provide a more complete picture for an attending physician during, and subsequent to, surgery. For example, the aforementioned elements or other elements are operative to generate data indicative of the presence of infection and the pressure exerted upon one or more predetermined surfaces of a prosthetic implant.

There are numerous possible applications for the present invention. For starters, the present invention is applicable to prosthetic surgeries involving joint replacement. It is to be understood that the present invention is not limited to joint replacement surgeries, and may be easily modified to impart the desired functionality for any operational endeavor or any external fixation device such as a smart brace. The exemplary disclosure as recited herein is also applicable to prosthetic trial components, thereby giving the surgeon substantially real-time information about pressure distributions prior to fitting the eventual implanted prosthesis. As a breakthrough technology, the present invention allows unparalleled synergy between previously unrelated fields such as biology and microelectronics to enable monitoring of conditions not previously monitorable without the associated risk of infection or other complications.

In exemplary form, the present invention includes a sensor array, associated with a prosthetic implant, that is operative to detect at least one of: viscosity of the synovial fluid; pH of the synovial fluid; cell count within the synovial fluid; protein within the synovial fluid; phospholipids within the synovial fluid; hyaluronic acid within the synovial fluid; leukocytes within the synovial fluid; neutrophils within the synovial fluid; bacterial deoxyribonucleic acid within the synovial fluid; antibodies within the synovial fluid; glucose concentration within the synovial fluid; lactate dehydrogenase (LDH) within the synovial fluid; uric acid crystals within the synovial fluid; MMP-9 antigens (gelatinase-B) within the synovial fluid; nerve growth factor within the synovial fluid; excitatory amino acids (EAA) glutamate and aspartate within the synovial fluid; insulin-like growth factor I (IGF-I) and its binding proteins (IGFBP) 3 and 4 within the synovial fluid; oxidase activity within the synovial fluid; polyamine oxidases within the synovial fluid; caeruloplasmin (Cp) concentration within the synovial fluid; beta-glucuronidase content within the synovial fluid; S100A8/A9 within the synovial fluid; C reactive protein within the synovial fluid; rheumatoid factor within the synovial fluid; C3 and C4 within the synovial fluid; metal particulate within the synovial fluid; polyethylene particulate within the synovial fluid; bone particulate within the synovial fluid; cement particulate within the synovial fluid; osteolytic enzymes within the synovial fluid; genetic markers within the synovial fluid; antibody markers within the synovial fluid; temperature of the synovial fluid; specific gravity of the synovial fluid; and white cells (and differential cell type) within the synovial fluid. The sensed condition is routed through a wireless transmitter and broadcast to a remote terminal. In a further exemplary embodiment, the sensor array and transmitter are integrated into a prosthetic device and subsequent to surgery, housed completely within the mammalian body. The data attributable to the sensor array is received by a remote terminal, which in exemplary form comprises a personal data assistant. A warning sign of early infection detection could be a configured to correspond to a predetermined sound, a predetermined frequency, or other signal.

The present invention is applicable outside of the summary examples recited above and reference is had to the remainder of the written description to more fully understand the scope and spirit of the present invention.

It is a first aspect of the present invention to provide a prosthesis for implantation into a mammalian body, the device comprising: (a) a prosthesis for implantation into a mammalian body that includes a sensor array comprising a plurality of sensors mounted to the prosthesis; and (b) an electronics structure for receiving signals from the sensor array and wirelessly transmitting representative signals to a remote receiver.

In a more detailed embodiment of the first aspect, the sensor array includes sensors detecting at least one of a predetermined component, a predetermined contaminant, and a predetermined property. In yet another more detailed embodiment, the plurality of sensors include at least one of an encapsulated sensor and a sensor in fluid communication with mammalian bodily fluids bathing the prosthesis. In a further detailed embodiment, the electronics structure includes a timing circuit configured to automatically activate the sensor array and to automatically deactivate the sensor array. In still a further detailed embodiment, the plurality of sensors include at least one of resistive microcantilevers, piezoelectric microcantilevers, and microcapacitor sensors. In a more detailed embodiment, the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trail hip replacement acetabular cup insert prosthesis. In a more detailed embodiment, the prosthesis includes a knee replacement femoral prosthesis and the sensor array is embedded within the knee replacement femoral prosthesis. In another more detailed embodiment, the prosthesis includes a knee replacement tibial prosthesis and the sensor array is embedded within the knee replacement tibial prosthesis. In yet another more detailed embodiment, the prosthesis includes a knee replacement tibial tray prosthesis and the sensor array is embedded within the knee replacement tibial tray prosthesis. In still another more detailed embodiment, the prosthesis includes a hip replacement femoral prosthesis and the sensor array is embedded within the hip replacement femoral prosthesis.

In yet another more detailed embodiment of the first aspect, the prosthesis includes a hip replacement acetabular cup prosthesis and the sensor array is embedded within the hip replacement acetabular cup prosthesis. In still another more detailed embodiment, the prosthesis includes a hip replacement acetabular cup insert prosthesis and the sensor array is embedded within the hip replacement acetabular cup insert prosthesis. In a further detailed embodiment, at least one of the plurality of sensors of the sensor array is operative to sense at least one of: leukocyte concentration, neutrophil concentration, bacterial deoxyribonucleic acid concentration, antibody concentration, glucose concentration, excitatory amino acids concentration, lactate dehydrogenase concentration, hyaluronic acid concentration, uric acid concentration, calcium pyrophosphate concentration, beta-glucuronidase concentration, nerve growth factor concentration, insulin-like growth factor concentration, Caeruloplasmin concentration, and oxidase concentration. In still a further detailed embodiment, at least one of the sensor array and the electronics structure is powered using at least one of electromagnetic induction, radio frequency induction, and battery power. In a more detailed embodiment, the electronics structure includes a microcontroller and a transmitter. In a more detailed embodiment, the electronics structure includes an application specific integrated circuit, which includes a filter for filtering out low frequency noise. In another more detailed embodiment, the electronics structure includes an application specific integrated circuit, which includes an amplifier for amplifying signals from the sensor array. In yet another more detailed embodiment, the electronics structure includes an application specific integrated circuit, which includes a multiplexer for multiplexing signals from the sensor array.

In yet another more detailed embodiment of the first aspect, the electronics structure includes an application specific integrated circuit, which includes an analog-to-digital converter for converting analog signals from the sensor array to digital signals. In still another more detailed embodiment, the electronics structure includes an application specific integrated circuit, which includes a processor for processing signals from the sensor array. In a further detailed embodiment, the sensors of the sensor array are operative to sense at least one of pressure and temperature. In still a further detailed embodiment, the prosthesis includes a microchannel and a micropump in communication with the microchannel to pump mammalian bodily fluid bathing the joint through the microchannel, where an interior of the microchannel is in communication with at least one of the plurality of sensors. In a more detailed embodiment, the wireless transmission of representative signals is accomplished using a radio frequency transmitter. In a more detailed embodiment, the plurality of sensors are operative to sense pressure changes in three axes of movement.

It is a second aspect of the present invention to provide a method of monitoring a prosthetic implant and its host mammalian body, the method comprising the steps of: (a) implanting a sensor array into the mammalian body, the sensor array accompanying a prosthesis also implanted into the mammalian body; (b) sensing a condition of at least one of a predetermined component, a predetermined contaminant, and a predetermined property using the sensor array; (c) generating signals responsive to the sensed condition; (d) wirelessly transmitting signals to a remote receiver outside of the mammalian body, the transmitted signals being representative of signals generated by the sensor array in response to sensing the condition; and (e) processing the transmitted signals by the remote receiver to generate data representative of the sensed condition.

In a more detailed embodiment of the first aspect, the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trail hip replacement acetabular cup insert prosthesis. In yet another more detailed embodiment, the invention also includes filtering out low frequency noise from the generated signals prior to the wirelessly transmitting step. In a further detailed embodiment, the invention also includes amplifying the generated signals prior to the wirelessly transmitting step. In still a further detailed embodiment, the invention also includes multiplexing the generated signals prior to the wirelessly transmitting step. In a more detailed embodiment, the invention also includes converting the generated signals from analog to digital prior to the wirelessly transmitting step. In a more detailed embodiment, the invention also includes processing the generated signals prior to the wirelessly transmitting step. In another more detailed embodiment, the step of sensing the condition includes sensing at least one of pressure and temperature. In yet another more detailed embodiment, the step of sensing the condition includes utilizing at least one of a microcantilever and a microcapacitor. In still another more detailed embodiment, the step of sensing the condition includes sensing for markers of infection.

In yet another more detailed embodiment of the first aspect, the step of sensing the condition includes encapsulated sensors responsive to pressure changes. In still another more detailed embodiment, the step of sensing the condition includes sensors in fluid communication with bodily fluids bathing the prosthesis. In a further detailed embodiment, the invention also includes displaying visual representations of the data generated by or during the processing step, and responding to the displayed visual representations to take appropriate corrective action where applicable. In still a further detailed embodiment, the step of sensing the condition includes the use of encapsulated sensors responsive to pressure changes. In a more detailed embodiment, the step of sensing the condition includes sensing at least one of: leukocyte concentration, neutrophil concentration, bacterial deoxyribonucleic acid concentration, antibody concentration, glucose concentration, excitatory amino acids concentration, lactate dehydrogenase concentration, hyaluronic acid concentration, uric acid concentration, calcium pyrophosphate concentration, beta-glucuronidase concentration, nerve growth factor concentration, insulin-like growth factor concentration, Caeruloplasmin concentration, and oxidase concentration It is a third aspect of the present invention to provide a method of detecting infection within mammalian body, the method comprising the steps of: (a) implanting a sensor array into the mammalian body, the sensor array accompanying a prosthesis also implanted into the mammalian body; (b) sensing for a marker representative of infection; (c) generating signals from the sensor array when the marker representative of infection is sensed; (d) wirelessly transmitting signals to a remote receiver outside of the mammalian body, the transmitted signals being representative of signals generated by the sensor array in response to sensing the marker; and (e) processing the transmitted signals by the remote receiver to generate data representative of the sensed marker.

It is a fourth aspect of the present invention to provide a method of detecting premature failure of a prosthetic implant in a host mammalian body, the method comprising the steps of: (a) implanting a sensor array into the mammalian body, the sensor array accompanying a prosthesis also implanted into the mammalian body; (b) sensing conditions comprising at least one of pressure and constituents of mammalian bodily fluid bathing the prosthesis; (c) generating signals responsive to the sensed conditions; (d) wirelessly transmitting signals to a remote receiver outside of the mammalian body, the transmitted signals being representative of signals generated by the sensor array in response to sensing the conditions; and (e) processing the transmitted signals by the remote receiver to generate data representative of the sensed condition.

It is a fifth aspect of the present invention to provide a method of fabricating a prosthesis, the method comprising: (a) associating a prosthetic component with a fluid conduit adapted to be in fluid communication with a mammalian bodily fluid bathing the prosthetic joint; and (b) orienting a plurality of sensors into fluid communication with the interior of the fluid conduit, where the sensors are operative to detect at least one of a predetermined component, a predetermined contaminant, and a predetermined property.

It is a sixth aspect of the present invention to provide a method of fabricating a sensor array, the method comprising: (a) mounting a plurality of microcantilevers sensors onto a substrate in a predetermined distribution; and (b) encapsulating the microcantilever sensors.

It is a seventh aspect of the present invention to provide a method of fabricating a sensor array, the method comprising: (a) fabricating a plurality of capacitive sensors a plurality of microcantilevers sensors onto a substrate in a predetermined distribution; and (b) encapsulating the microcantilever sensors.

It is an eighth seventh aspect of the present invention to provide an external brace for supplementing the support structure of a mammalian body, the device comprising: (a) an external brace for mounting to the exterior of a mammalian body, the brace including a sensor array mounted thereto; and (b) an electronics structure for receiving data from the sensor array and wirelessly transmitting representative data to a remote receiver.

It is a ninth aspect of the present invention to provide a sensor array comprising: (a) a first capacitive sensor comprising conductive plates separated by a dielectric material, the capacitive plates of the first capacitive sensor lying along a first X-Y and operative to detect pressure along the X axis; (b) a second capacitive sensor comprising conductive plates separated from one another, the capacitive plates of the second capacitive sensor lying along the first X-Y plane and operative to detect pressure along the Y axis; and (c) a third capacitive sensor comprising conductive plates separated from one another, the capacitive plates of the third capacitive sensor lying along the first X-Y plane and operative to detect pressure along a Z plane orthogonal to the first X-Y plane.

It is a tenth aspect of the present invention to provide a prosthetic trial implant having a microcantilevered sensor array integral to the prosthetic trial implant and operatively coupled to a transmitter to communicate sensed data to a remote transmitter, where the sensed data is indicative of current conditions of a fluid in communication with at least one sensor of the sensor array.

It is an eleventh aspect of the present invention to provide a prosthesis having a microcantilevered sensor array integral to the prosthetic permanent implant and operatively coupled to a transmitter to communicate sensed data to a remote transmitter, the sensor array and transmitter including inductively powered and operative to detect at least one of temperature, pressure, and pH of a fluid in communication with at least one sensor of the sensor array.

It is a twelfth aspect of the present invention to provide a prosthetic implant including a microelectromechanical controller coupled to a microcantilevered sensor array integral to the prosthetic implant and operative to sense environmental conditions relative to the prosthetic implant to detect wear of the prosthetic implant more than three months subsequent to a prosthetic implant surgery and provide data to a remote data receiving device operative to allow a physician to determine whether adjustments and/or surgical repair is warranted.

It is a thirteenth aspect of the present invention to provide a prosthetic implant comprising: (a) a prosthetic support structure operative to be mounted to a preexisting support structure of a mammalian body; (b) a sensor array having a plurality of sensors, where at least one of the sensors is operative to detect at least one of viscosity of the synovial fluid; pH of the synovial fluid; cell count within the synovial fluid; protein within the synovial fluid; phospholipids within the synovial fluid; hyaluronic acid within the synovial fluid; leukocytes within the synovial fluid; neutrophils within the synovial fluid; bacterial deoxyribonucleic acid within the synovial fluid; antibodies within the synovial fluid; glucose concentration within the synovial fluid; lactate dehydrogenase (LDH) within the synovial fluid; uric acid crystals within the synovial fluid; MMP-9 antigens (gelatinase-B) within the synovial fluid; nerve growth factor within the synovial fluid; excitatory amino acids (EAA) glutamate and aspartate within the synovial fluid; insulin-like growth factor I (IGF-I) and its binding proteins (IGFBP) 3 and 4 within the synovial fluid; oxidase activity within the synovial fluid; polyamine oxidases within the synovial fluid; caeruloplasmin (Cp) concentration within the synovial fluid; beta-glucuronidase content within the synovial fluid; S100A8/A9 within the synovial fluid; C reactive protein within the synovial fluid; rheumatoid factor within the synovial fluid; C3 and C4 within the synovial fluid; metal particulate within the synovial fluid; polyethylene particulate within the synovial fluid; bone particulate within the synovial fluid; cement particulate within the synovial fluid; osteolytic enzymes within the synovial fluid; genetic markers within the synovial fluid; antibody markers within the synovial fluid; temperature of the synovial fluid; specific gravity of the synovial fluid; and white cells (and differential cell type) within the synovial fluid; and (c) a transmitter in electrical communication with at least one sensor of the sensor array and operative to transmit data to a remote receive indicative of at least one of viscosity of the synovial fluid; pH of the synovial fluid; cell count within the synovial fluid; protein within the synovial fluid; phospholipids within the synovial fluid; hyaluronic acid within the synovial fluid; leukocytes within the synovial fluid; neutrophils within the synovial fluid; bacterial deoxyribonucleic acid within the synovial fluid; antibodies within the synovial fluid; glucose concentration within the synovial fluid; lactate dehydrogenase (LDH) within the synovial fluid; uric acid crystals within the synovial fluid; MMP-9 antigens (gelatinase-B) within the synovial fluid; nerve growth factor within the synovial fluid; excitatory amino acids (EAA) glutamate and aspartate within the synovial fluid; insulin-like growth factor I (IGF-I) and its binding proteins (IGFBP) 3 and 4 within the synovial fluid; oxidase activity within the synovial fluid; polyamine oxidases within the synovial fluid; caeruloplasmin (Cp) concentration within the synovial fluid; beta-glucuronidase content within the synovial fluid; S100A8/A9 within the synovial fluid; C reactive protein within the synovial fluid; rheumatoid factor within the synovial fluid; C3 and C4 within the synovial fluid; metal particulate within the synovial fluid; polyethylene particulate within the synovial fluid; bone particulate within the synovial fluid; cement particulate within the synovial fluid; osteolytic enzymes within the synovial fluid; genetic markers within the synovial fluid; antibody markers within the synovial fluid; temperature of the synovial fluid; specific gravity of the synovial fluid; and white cells (and differential cell type) within the synovial fluid.

It is a fourteenth aspect of the present invention to provide a prosthesis for implantation into a mammalian body, the device comprising: (a) a prosthesis for implantation into a mammalian body that includes a sensor array comprising a plurality of sensors mounted to the prosthesis; and (b) an electronics structure for receiving signals from the sensor array and wirelessly transmitting representative signals to a remote receiver where the plurality of sensors are operative to sense pressure, applied to the prosthesis by another object, in at least two axes generally perpendicular to one another.

In a more detailed embodiment of the fourteenth aspect, the electronics structure includes a timing circuit configured to automatically activate the sensor array and to automatically deactivate the sensor array. In yet another more detailed embodiment, the plurality of sensors include at least one of resistive microcantilevers, piezoelectric microcantilevers, and microcapacitor sensors. In a further detailed embodiment, the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trail hip replacement acetabular cup insert prosthesis. In still a further detailed embodiment, at least one of the sensor array and the electronics structure is powered using at least one of electromagnetic induction, radio frequency induction, and battery power. In a more detailed embodiment, the electronics structure includes a microcontroller and a transmitter. In a more detailed embodiment, the electronics structure includes an application specific integrated circuit, which includes a filter for filtering out low frequency noise. In another more detailed embodiment, the electronics structure includes an application specific integrated circuit, which includes an amplifier for amplifying signals from the sensor array. In yet another more detailed embodiment, the electronics structure includes an application specific integrated circuit, which includes a multiplexer for multiplexing signals from the sensor array. In still another more detailed embodiment, the electronics structure includes an application specific integrated circuit, which includes an analog-to-digital converter for converting analog signals from the sensor array to digital signals.

In yet another more detailed embodiment of the fourteenth aspect, the electronics structure includes an application specific integrated circuit, which includes a processor for processing signals from the sensor array. In still another more detailed embodiment, at least one of the plurality of sensors is operative to sense temperature. In a further detailed embodiment, the prosthesis includes a microchannel and a micropump in communication with the microchannel to pump mammalian bodily fluid bathing the joint through the microchannel, where an interior of the microchannel is in communication with at least one of the plurality of sensors.

It is a fifteenth aspect of the present invention to provide a prosthesis for implantation into a mammalian body, the device comprising: (a) a prosthesis for implantation into a mammalian body that includes a sensor array comprising a plurality of sensors mounted to the prosthesis; and (b) an electronics structure for receiving signals from the sensor array and wirelessly transmitting representative signals to a remote receiver, where at least one of the plurality of sensors is in fluid communication with fluids bathing the prosthesis.

In a more detailed embodiment of the fifteenth aspect, the sensor array includes sensors detecting at least one of a predetermined component, a predetermined contaminant, and a predetermined property. In yet another more detailed embodiment, the electronics structure includes a timing circuit configured to automatically activate the sensor array and to automatically deactivate the sensor array. In a further detailed embodiment, the plurality of sensors include at least one of resistive microcantilevers, piezoelectric microcantilevers, and microcapacitor sensors. In still a further detailed embodiment, the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trail hip replacement acetabular cup insert prosthesis. In a more detailed embodiment, at least one of the plurality of sensors of the sensor array is operative to sense at least one of: leukocyte concentration, neutrophil concentration, bacterial deoxyribonucleic acid concentration, antibody concentration, glucose concentration, excitatory amino acids concentration, lactate dehydrogenase concentration, hyaluronic acid concentration, uric acid concentration, calcium pyrophosphate concentration, beta-glucuronidase concentration, nerve growth factor concentration, insulin-like growth factor concentration, Caeruloplasmin concentration, and oxidase concentration.

In yet another more detailed embodiment of the fifteenth aspect, at least one of the sensor array and the electronics structure is powered using at least one of electromagnetic induction, radio frequency induction, and battery power. In still another more detailed embodiment, the electronics structure includes a microcontroller and a transmitter. In a further detailed embodiment, the electronics structure includes an application specific integrated circuit, which includes a filter for filtering out low frequency noise. In still a further detailed embodiment, the electronics structure includes an application specific integrated circuit, which includes an amplifier for amplifying signals from the sensor array. In a more detailed embodiment, the electronics structure includes an application specific integrated circuit, which includes a multiplexer for multiplexing signals from the sensor array. In a more detailed embodiment, the electronics structure includes an application specific integrated circuit, which includes an analog-to-digital converter for converting analog signals from the sensor array to digital signals. In another more detailed embodiment, the electronics structure includes an application specific integrated circuit, which includes a processor for processing signals from the sensor array. In yet another more detailed embodiment, the prosthesis includes a microchannel and a micropump in communication with the microchannel to pump mammalian bodily fluid bathing the joint through the microchannel, where an interior of the microchannel is in communication with at least one of the plurality of sensors. In yet a further more detailed embodiment, the wireless transmission of representative signals is accomplished using a radio frequency transmitter.

It is a sixteenth aspect of the present invention to provide a method of monitoring a prosthetic implant and its host mammalian body, the method comprising the steps of: (a) implanting a sensor array into the mammalian body, the sensor array mounted to a prosthesis also implanted into the mammalian body; (b) sensing pressure applied to the prosthesis in at least two axes generally perpendicular to one another; (c) generating signals responsive to the sensed pressure applied to the prosthesis by another object; and (d) wirelessly transmitting signals to a remote receiver outside of the mammalian body, the transmitted signals being representative of signals generated by the sensor array in response to sensing the pressure.

In a more detailed embodiment of the sixteenth aspect, the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trail hip replacement acetabular cup insert prosthesis. In yet another more detailed embodiment, the method also includes filtering out low frequency noise from the generated signals prior to the wirelessly transmitting step. In a further detailed embodiment, the method also includes amplifying the generated signals prior to the wirelessly transmitting step. In still a further detailed embodiment, the method also includes multiplexing the generated signals prior to the wirelessly transmitting step. In a more detailed embodiment, the method further includes converting the generated signals from analog to digital prior to the wirelessly transmitting step. In a more detailed embodiment, the method further includes processing the generated signals prior to the wirelessly transmitting step. In another more detailed embodiment, the step of sensing the condition includes sensing at least one of pressure and temperature. In yet another more detailed embodiment, the step of sensing the condition includes utilizing at least one of a microcantilever and a microcapacitor. In still another more detailed embodiment, the step of sensing the condition includes sensing for markers of infection.

In yet another more detailed embodiment of the sixteenth aspect, the step of sensing the condition includes encapsulated sensors responsive to pressure changes. In still another more detailed embodiment, the step of sensing the condition includes sensors in fluid communication with bodily fluids bathing the prosthesis. In a further detailed embodiment, the method further includes displaying visual representations of the data generated by or during the processing step, and responding to the displayed visual representations to take appropriate corrective action where applicable. In still a further detailed embodiment, the step of sensing the condition includes the use of encapsulated sensors responsive to pressure changes. In a more detailed embodiment, the step of sensing the condition includes sensing at least one of: leukocyte concentration, neutrophil concentration, bacterial deoxyribonucleic acid concentration, antibody concentration, glucose concentration, excitatory amino acids concentration, lactate dehydrogenase concentration, hyaluronic acid concentration, uric acid concentration, calcium pyrophosphate concentration, beta-glucuronidase concentration, nerve growth factor concentration, insulin-like growth factor concentration, Caeruloplasmin concentration, and oxidase concentration. In a more detailed embodiment, the method further includes processing the transmitted signals by the remote receiver to generate data representative of the sensed pressure.

It is a seventeenth aspect of the present invention to provide a method of monitoring a prosthetic implant and its host mammalian body, the method comprising the steps of: (a) implanting a sensor array into the mammalian body, the sensor array mounted to a prosthesis also implanted into the mammalian body, where at least one sensor of the sensor array is in fluid communication with fluids bathing the prosthesis; (b) sensing a condition of at least one of a predetermined component, a predetermined contaminant, and a predetermined property using the sensor array; (c) generating signals responsive to the sensed condition; and (d) wirelessly transmitting signals to a remote receiver outside of the mammalian body, the transmitted signals being representative of signals generated by the sensor array in response to sensing the condition.

In a more detailed embodiment of the seventeenth aspect, the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trail hip replacement acetabular cup insert prosthesis. In yet another more detailed embodiment, the method further comprises filtering out low frequency noise from the generated signals prior to the wirelessly transmitting step. In a further detailed embodiment, the method further comprises amplifying the generated signals prior to the wirelessly transmitting step. In still a further detailed embodiment, the method further comprises multiplexing the generated signals prior to the wirelessly transmitting step. In a more detailed embodiment, the method further comprises converting the generated signals from analog to digital prior to the wirelessly transmitting step. In a more detailed embodiment, the method further comprises processing the generated signals prior to the wirelessly transmitting step. In another more detailed embodiment, the step of sensing the condition includes sensing at least one of pressure and temperature. In yet another more detailed embodiment, the step of sensing the condition includes utilizing at least one of a microcantilever and a microcapacitor. In still another more detailed embodiment, the step of sensing the condition includes sensing for markers of infection.

In yet another more detailed embodiment of the seventeenth aspect, the step of sensing the condition includes encapsulated sensors responsive to pressure changes. In still another more detailed embodiment, the step of sensing the condition includes sensors in fluid communication with bodily fluids bathing the prosthesis. In a further detailed embodiment, the method further comprises displaying visual representations of the data generated by or during the processing step, and responding to the displayed visual representations to take appropriate corrective action where applicable. In still a further detailed embodiment, the step of sensing the condition includes the use of encapsulated sensors responsive to pressure changes. In a more detailed embodiment, the step of sensing the condition includes sensing at least one of: leukocyte concentration, neutrophil concentration, bacterial deoxyribonucleic acid concentration, antibody concentration, glucose concentration, excitatory amino acids concentration, lactate dehydrogenase concentration, hyaluronic acid concentration, uric acid concentration, calcium pyrophosphate concentration, beta-glucuronidase concentration, nerve growth factor concentration, insulin-like growth factor concentration, Caeruloplasmin concentration, and oxidase concentration. In a more detailed embodiment, the method further comprises processing the transmitted signals by the remote receiver to generate data representative of the sensed condition.

It is an eighteenth aspect of the present invention to provide a method of fabricating a prosthesis, the method comprising: (a) fabricating a prosthesis with a fluid conduit adapted to be in fluid communication with a mammalian bodily fluid bathing the prosthetic joint; and (b) orienting a plurality of sensors into fluid communication with the interior of the fluid conduit, where the sensors are operative to detect at least one of a predetermined component, a predetermined contaminant, and a predetermined property.

It is a nineteenth aspect of the present invention to provide a sensor array comprising: (a) a first capacitive sensor comprising conductive plates separated by a dielectric material, the capacitive plates of the first capacitive sensor lying along a first X-Y and operative to detect pressure along the X axis; (b) a second capacitive sensor comprising conductive plates separated from one another, the capacitive plates of the second capacitive sensor lying along the first X-Y plane and operative to detect pressure along the Y axis; and (c) a third capacitive sensor comprising conductive plates separated from one another, the capacitive plates of the third capacitive sensor lying along the first X-Y plane and operative to detect pressure along a Z plane orthogonal to the first X-Y plane.

It is a twentieth aspect of the present invention to provide a prosthetic implant comprising: (a) a prosthetic sensor array mounted to a prosthesis, the sensor array including at least one sensor in fluid communication with a fluid surrounding the prosthesis subsequent to implanting the prosthesis into a mammalian body, where the at least one sensor is operative to detect at least one of the following properties: viscosity of the synovial fluid; pH of the synovial fluid; cell count within the synovial fluid; protein within the synovial fluid; phospholipids within the synovial fluid; hyaluronic acid within the synovial fluid; leukocytes within the synovial fluid; neutrophils within the synovial fluid; bacterial deoxyribonucleic acid within the synovial fluid; antibodies within the synovial fluid; glucose concentration within the synovial fluid; lactate dehydrogenase (LDH) within the synovial fluid; uric acid crystals within the synovial fluid; MMP-9 antigens (gelatinase-B) within the synovial fluid; nerve growth factor within the synovial fluid; excitatory amino acids (EAA) glutamate and aspartate within the synovial fluid; insulin-like growth factor I (IGF-I) and its binding proteins (IGFBP) 3 and 4 within the synovial fluid; oxidase activity within the synovial fluid; polyamine oxidases within the synovial fluid; caeruloplasmin (Cp) concentration within the synovial fluid; beta-glucuronidase content within the synovial fluid; S100A8/A9 within the synovial fluid; C reactive protein within the synovial fluid; rheumatoid factor within the synovial fluid; C3 and C4 within the synovial fluid; metal particulate within the synovial fluid; polyethylene particulate within the synovial fluid; bone particulate within the synovial fluid; cement particulate within the synovial fluid; osteolytic enzymes within the synovial fluid; genetic markers within the synovial fluid; antibody markers within the synovial fluid; temperature of the synovial fluid; specific gravity of the synovial fluid; and white cells (and differential cell type) within the synovial fluid; and (b) a transmitter in electrical communication with the at least one sensor of the sensor array and operative to transmit data to a remote receive indicative of at least one sensed property.

DETAILED DESCRIPTION

The exemplary embodiments of the present invention are described and illustrated below to encompass miniature sensors for use in the healthcare industry, such as sensors for use with prosthetic implants and prosthetic trials. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referencing FIGS. 1-6, a first exemplary embodiment of the present invention includes a prosthetic knee joint for use with a total knee arthroplasty procedure. The knee joint comprises a tibial tray 12, a tray insert 14, and a femoral prosthesis 16. The interaction and assembly of simple tibial trays, tray inserts, and femoral prostheses are well known to those skilled in the art. Consistent with the interaction of these simple prosthetic components, the exemplary components 12, 14, 16 of the knee joint of the present invention integrate and function as a replacement knee joint without compromising the primary functionality of the joint itself.

Figure 1:
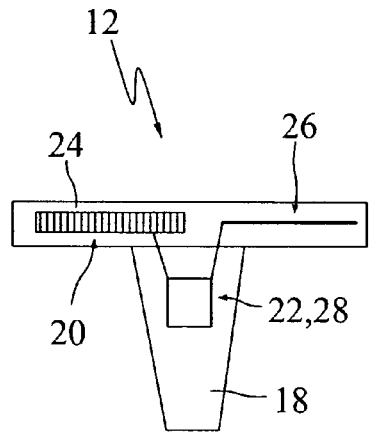
FIG. 1 is a frontal view of an exemplary tibial tray in accordance with the present invention.
Figure 2:
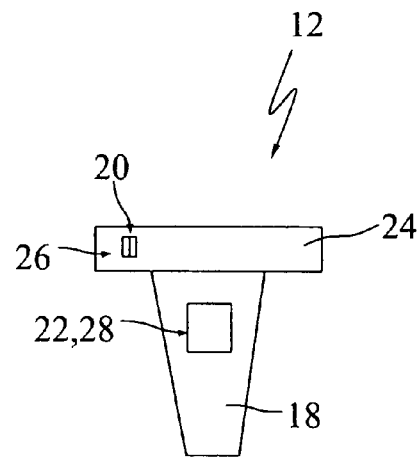
FIG. 2 is a left side view of the exemplary tibial tray of FIG. 1.

Referring specifically to FIGS. 1 and 2, the tibial tray 12 includes a downwardly extending shaft 18 mounted to a horizontal platform 24. The vertical shaft 18 houses an encoding and modulation device (EMD) 28 in communication with a microtransmitter 22. A sensor array 20 is mounted to the horizontal platform 24 that is also in communication with the EMD 28. An antenna 26 is mounted to the horizontal platform 24 and in communication with the microtransmitter 22, which receives signals from the EMD 28 to be transmitted to a remote electronic receiver (not shown). The sensor array 20 is distributed over the relevant areas of the platform 24 to effectively map those areas of the platform 24 contacted by the tray insert 14. The sensor array 20 may also include sensors adapted to sense components, contaminants, and properties exhibited by bodily fluids that surround the joint 10 subsequent to implantation. Regardless of the sensors utilized and particular data generated, detection data is communicated to the EMD 28, which in turn communicates data to the microtransmitter 22 that wirelessly transmits data using the antenna 32 to a remote electronic receiver 91 (see FIG. 25). Exemplary remote electronic receivers 91 include, without limitation, microcontroller based electronics such as a wireless telephone, a wireless personal data assistant, a personal computer, whether or not the electronic component includes a visual display. In an exemplary scenario, the remote receiver digital processes the signal from the implanted transmitter to generate a 3D graph that displays the load distribution on the sensing surface, as well as composition profiles for predetermined components, contaminants, and properties (see FIGS. 26-28).

Figure 3:
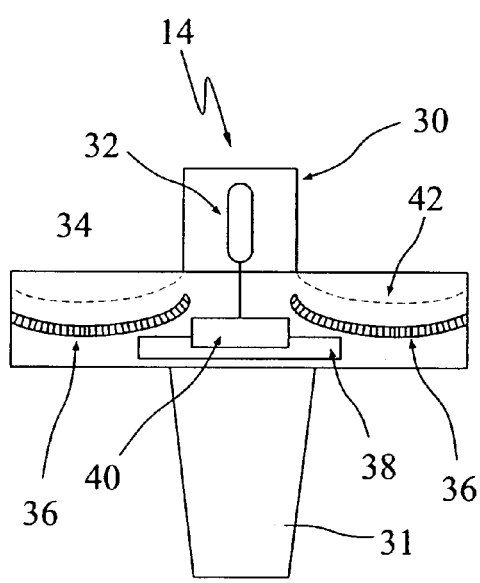
FIG. 3 is a frontal view of an exemplary tibial tray insert in accordance with the present invention.
Figure 4:
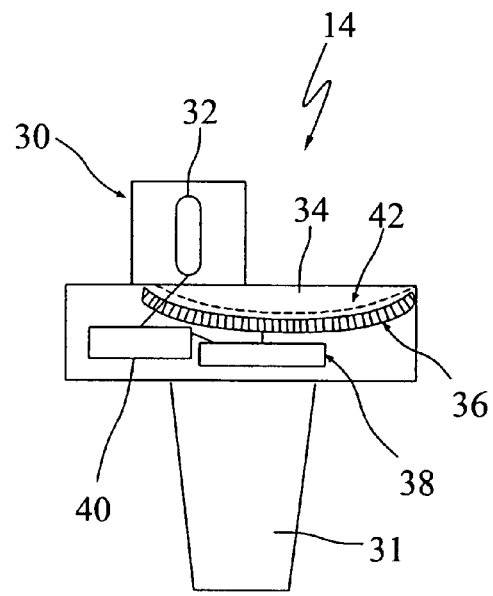
FIG. 4 is a left side view of the exemplary tibial tray insert of FIG. 3.

Referencing FIGS. 3 and 4, the tibial insert 14 includes an upper vertical post 30 extending from a base 34 opposite that of a lower vertical post 31 (in some tibial inserts the lower vertical post 31 may be absent). The upper vertical post 30 includes an antenna 32 in communication with a microtransmitter 40 housed within the base 34, as well as a sensor array 36 and an EMD 38 also mounted within the base 34. The base 34 is contoured to include a pair of articular surfaces 42 adapted to receive the condyles 50 of the femoral prosthesis 16 (see FIGS. 5 and 6). Some of the sensors of the array 36 are positioned underneath the articular surfaces 42 in a predetermined manner that operates to map the relevant areas of the articular surfaces 42 that will be contacted by the condyles 50 throughout the range of movement of the joint 10 to generate data representative of a pressure map across the articular surfaces 42. The sensor array 36 also may include sensors that detect certain components, contaminants, and properties relevant to the joint 10 (see [0076]-[0077], for example) and generate detection data representative of the component, contaminant, or property detected. The detection data generated by the sensors of the array 36, whether pressure related or otherwise, is communicated to the EMD 38, which in turn communicates data to the microtransmitter 40 that wirelessly transmits data using the antenna 32 to a remote electronic receiver 91 (see FIG. 25).

Figure 5:
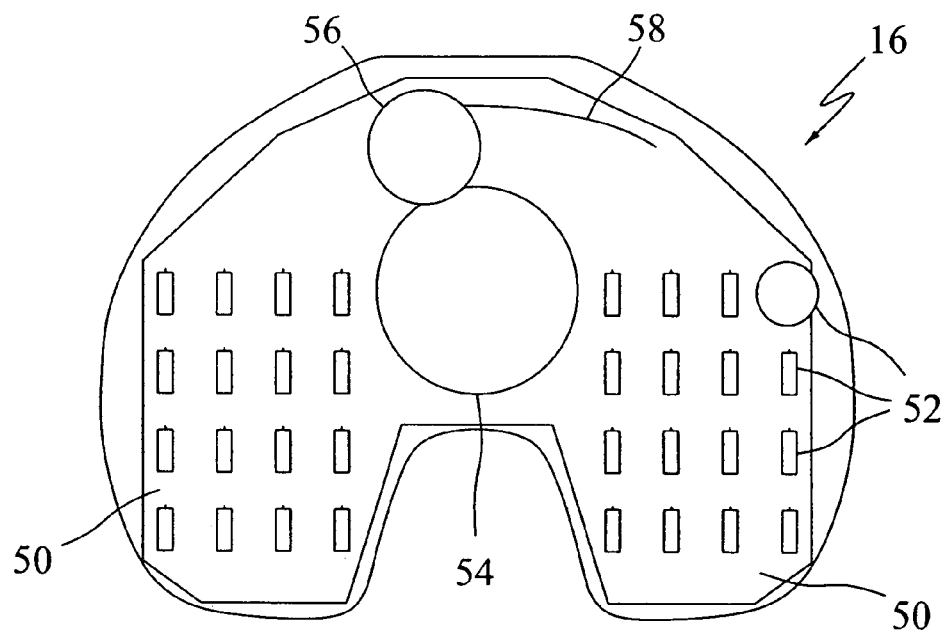
FIG. 5 is a top view of an exemplary femoral prosthesis in accordance with the present invention.
Figure 6:
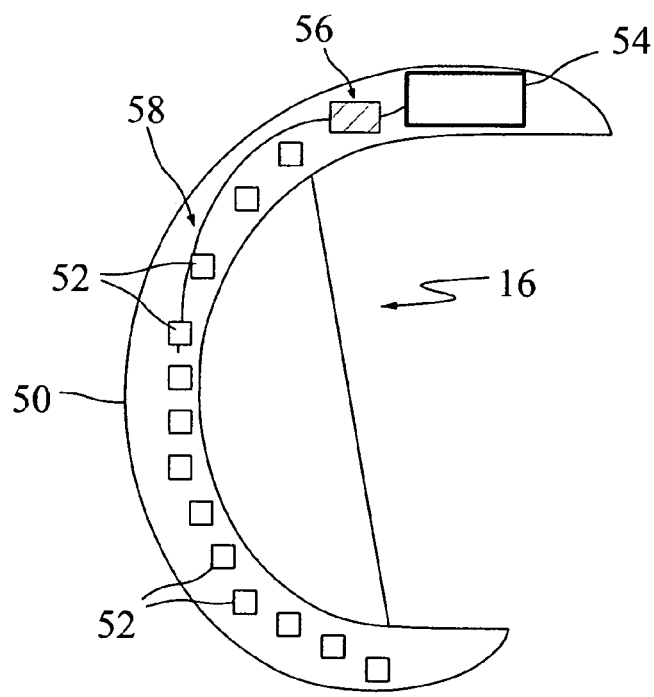
FIG. 6 is a left side view of the exemplary femoral prosthesis of FIG. 5.

Referencing FIGS. 5 and 6, the femoral prosthesis 16 includes a pair of U-shaped condyles 50 having a sensor array 52 in communication with an EMD 54, a microtransmitter 56, and an antenna 58. Numerous sensors of the array 52 are mounted to the condyles 50 to detect pressures exerted against the condyles, whereas other sensors within the array 52 may be adapted to be in fluid communication with the bodily fluids surrounding the joint 10 subsequent to the femoral prosthesis 16 being implanted. Those sensors of the array 52 that are in fluid communication with the bodily fluids surrounding the joint are operative to detect certain components, contaminants, and properties relevant to the joint 10 (see [0076]-[0077], for example) and generate detection data representative of the component, contaminant, or property detected. All of the detection data generated by the sensors of the array 52, whether pressure related or otherwise, is communicated to the EMD 54. The EMD 54 manipulates this data prior to communicating it to the microtransmitter 56 that wirelessly transmits data using the antenna 58 to a remote electronic receiver 91.

Figure 7:
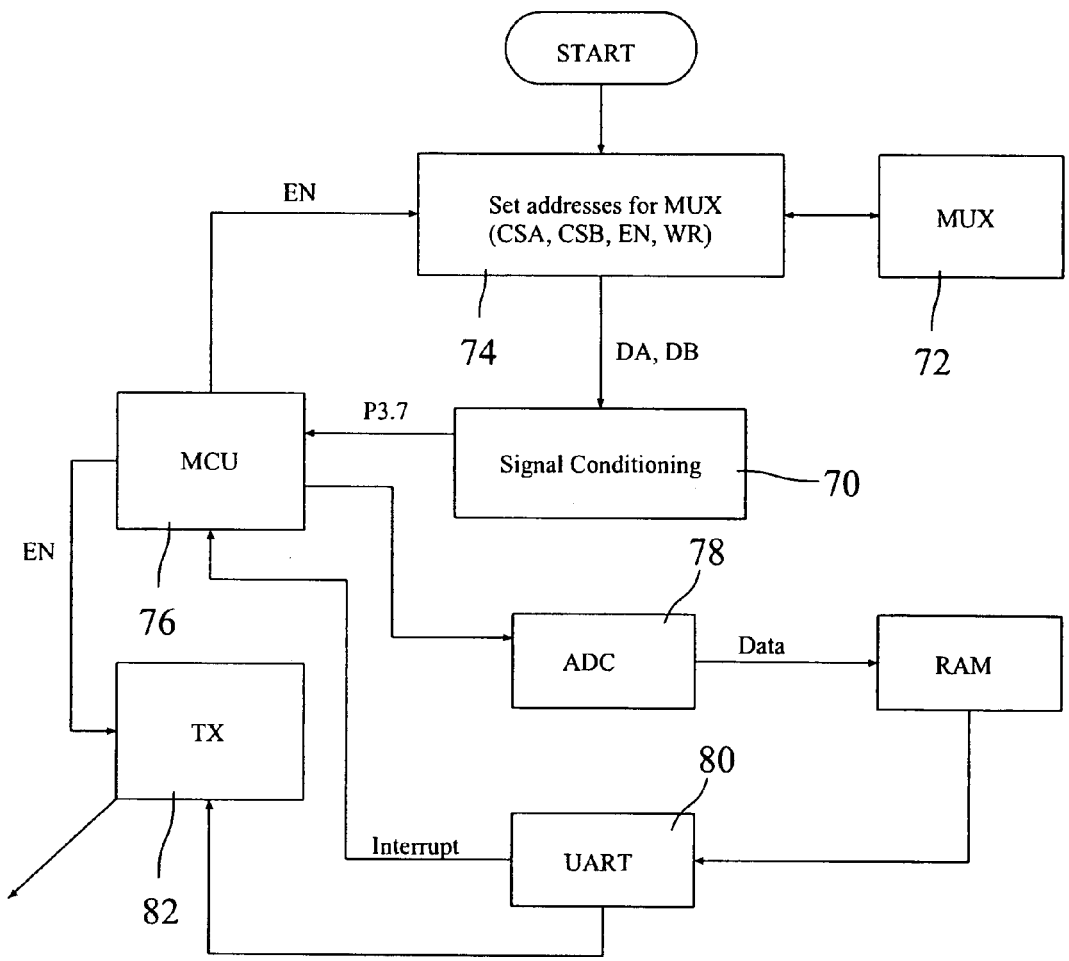
FIG. 7 is an exemplary schematic representation of the electronic functions carried out by the exemplary control electronics of the present invention.
Figure 8:
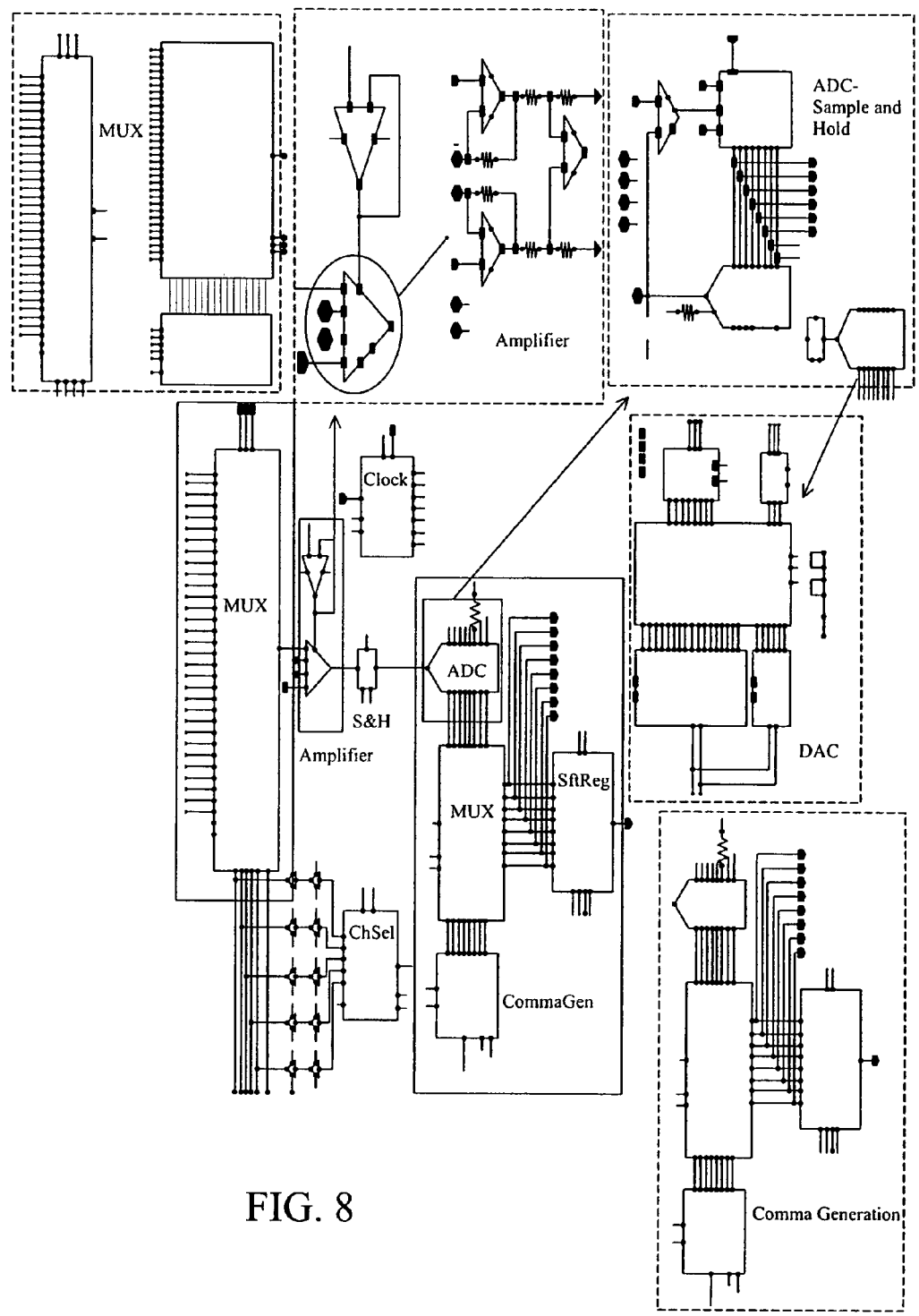
FIG. 8 is a wiring diagram of the electronics in communication with the sensors of the first exemplary embodiment of the present invention.
Figure 9:
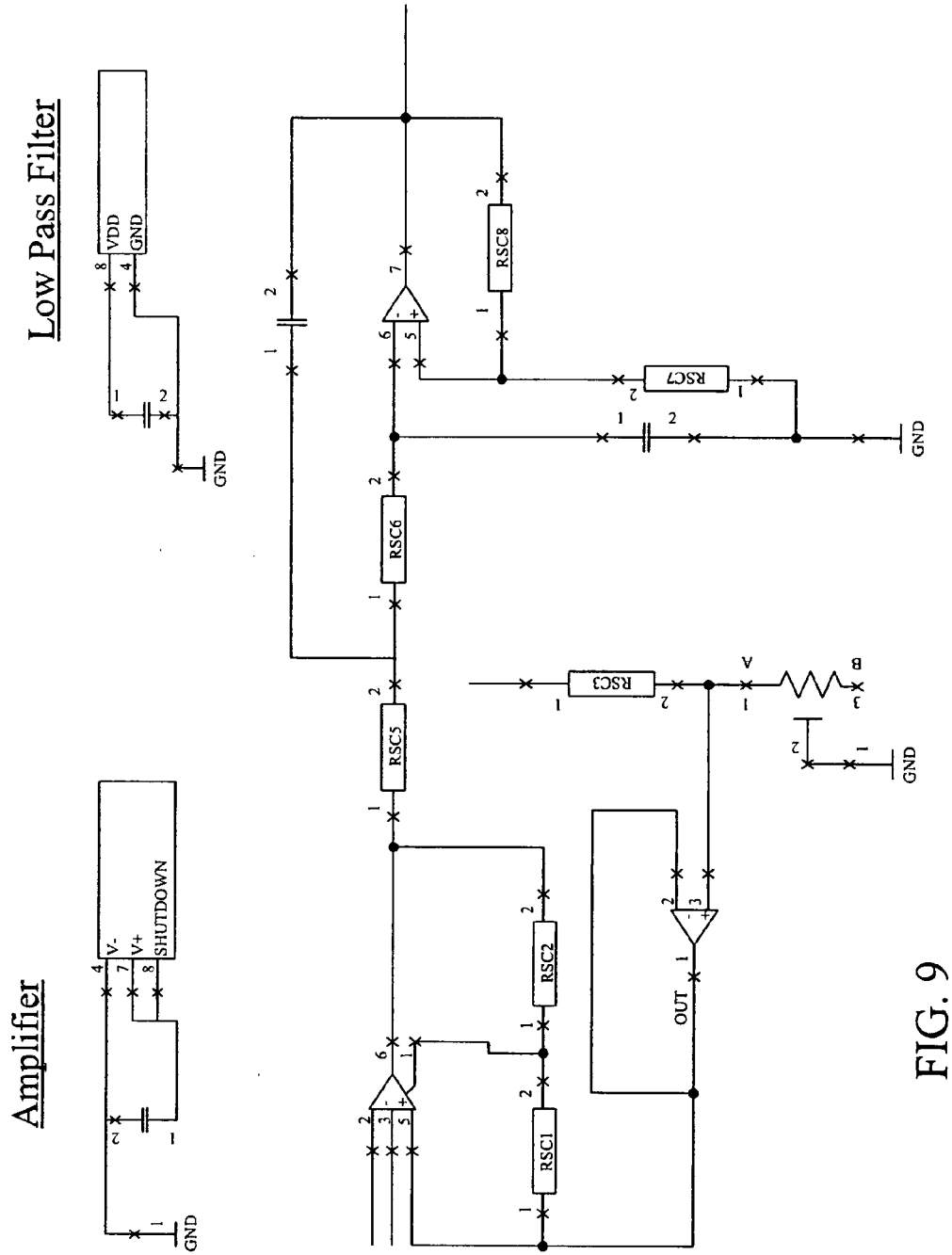
FIG. 9 is a wiring diagram of the amplifier and low pass filter in accordance with the first exemplary embodiment of the present invention.

Referring to FIGS. 7 and 8, the EMDs 28, 38, 54 of the exemplary embodiments comprise ultra low-power, Application Specific Integrated Circuit (ASIC) or System on Chip (SOC) that includes, as will be described in detail below, signal detection and amplification functionality, anti-alias filtering functionality, multiplexing functionality, analog to digital conversion functionality, data processing functionality and transmission functionality. The SOC is programmed in accordance with the flowchart of FIG. 7 and designed for battery powering, such as a coin cell battery. A schematic diagram of the SOC is shown in FIG. 8, with the aforementioned component functions discussed in more detail below.

Signal Conditioning and Amplification

Generally, the output signal of each sensor is very small. In this regard, it is important to include a circuit 70 that filters out low frequency noise and amplifies the desired signal with an instrumentation amplifier into the SOC. The gain of the amplifier is adjustable with one off-chip resistor.

Analog Multiplexer

In order to obtain information of each sensor, an analog multiplexer (MUX) 72 is utilized between a readout circuit 74 and the signal conditioning circuit 70 of the system. The MUX 72 acts as a switch controlled by signals sent to the decoder from the microcontroller (MCU) 76. In exemplary form, the MUX 72 uses five addressing signals to select one channel at a time from numerous (such as 30) channels sequentially. The ON-resistance among these numerous channels should be matched to increase the MUX 72 static accuracy. In order to work in a high-speed mode, the ON-resistance should be relatively small, which, in turn, may lead to large chip size. Those of ordinary skill will understand the implications when trading off between speed and die area.

Analog to Digital Conversion (ADC)

An 8-bit SAR ADC 78 was implemented in the exemplary SOC. Although Successive Approximation Register (SAR) ADC is a more complex analog-to-digital converting technique than digital ramp ADC, the former is much faster and the sampling time does not necessarily depend on the input voltage. An important part of the ADC 78 is a high resolution comparator, which has the ability to distinguish the minimum triggering signal with common mode voltage changing from 100 mV to 2 V. Consequentially, the SOC includes 256 quantization levels with precision of 7.4 mV. It is also important to match the 256 current sources to maintain good Integrated Non-Linearity (INL) and Differential Non-Linearity (DNL).

Data Processing

A comma generator and polarity check 80 are included with the SOC to facilitate distinguishing received data with their corresponding channels, as well as to facilitate detection of transmission errors. In exemplary form, an 8 bit start comma is sent prior to the signals from the first channel, and an end comma is sent after the last channel (channel 30, for example) signal. Thus, the receiver can check the received data's polarity to ensure the validity.

Transmitter

The transmitter 82 uses Amplitude Shift Keying (ASK) modulation with a carrier frequency at 433.92 MHz. As a result of potential inconsistencies in the Wheatstone bridge circuit, a feedback circuit with an off sensor is included with the SOC to ensure that it is balanced at all times.

Figure 10:
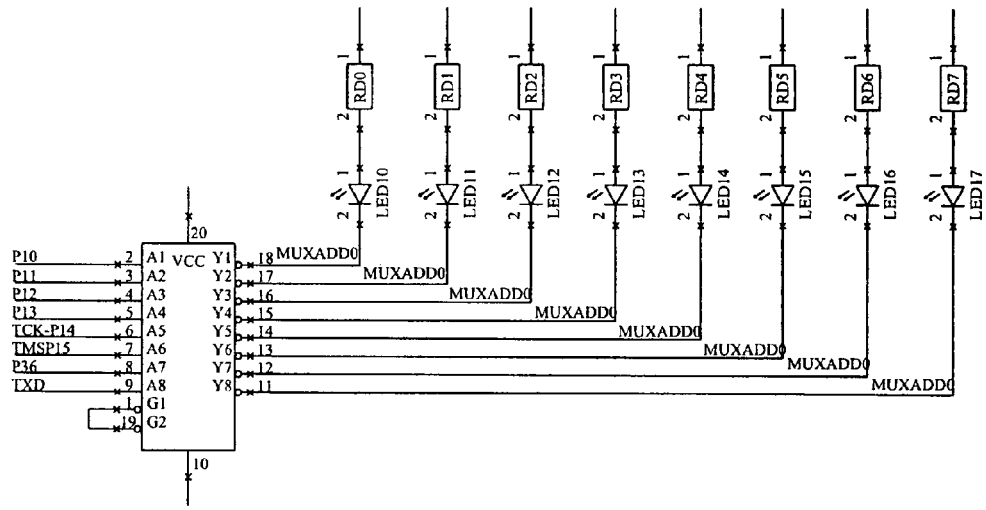
FIG. 10 is a wiring diagram of the feedback display in accordance with the first exemplary embodiment of the present invention.
Figure 11:
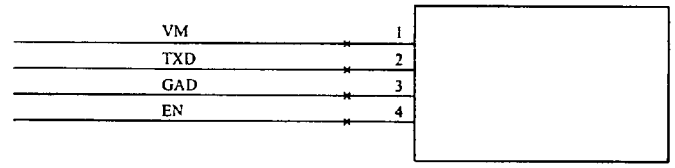
FIG. 11 is a wiring diagram of the interface with the transmitter in accordance with the first exemplary embodiment of the present invention.
Figure 12:
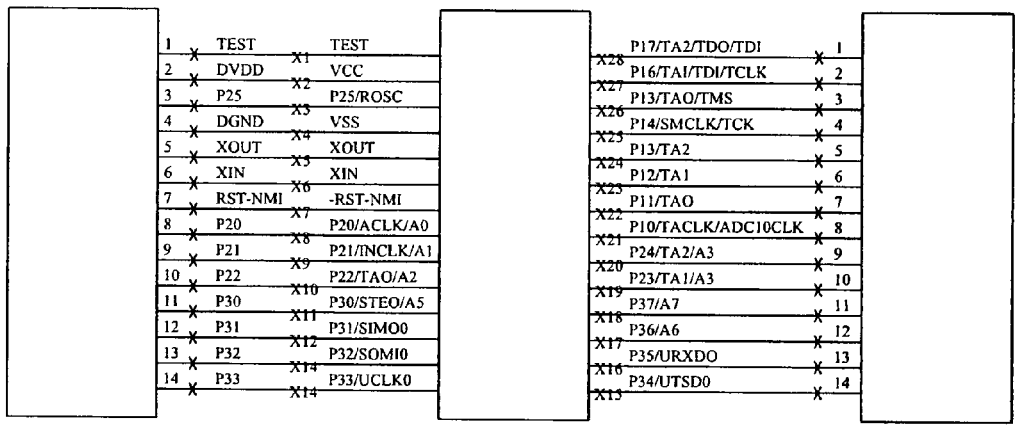
FIG. 12 is a wiring diagram of the microcontroller in accordance with the first exemplary embodiment of the present invention.
Figure 13:
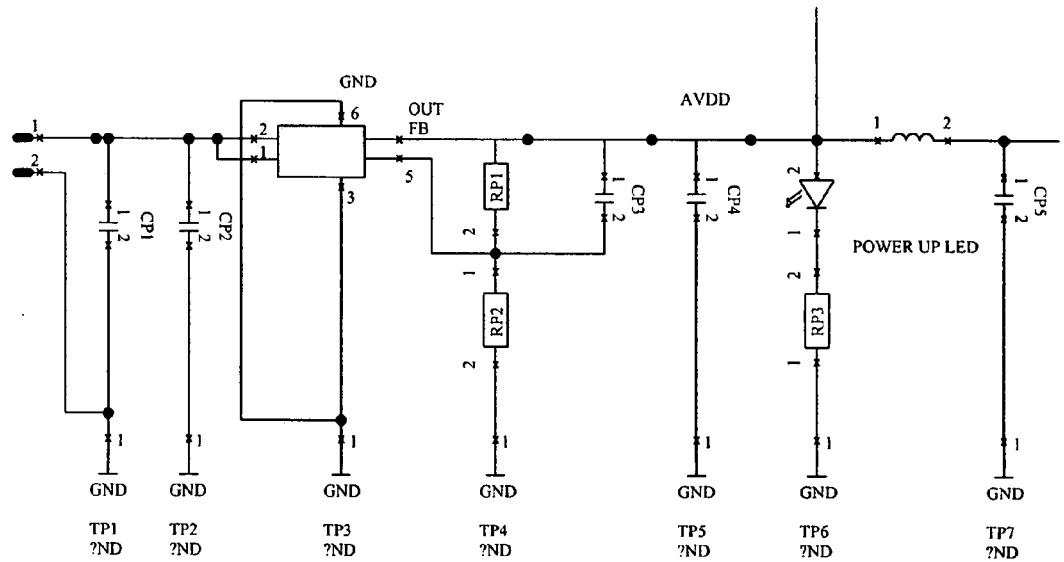
FIG. 13 is a wiring diagram of the power management hardware in accordance with the first exemplary embodiment of the present invention.
Figure 14:
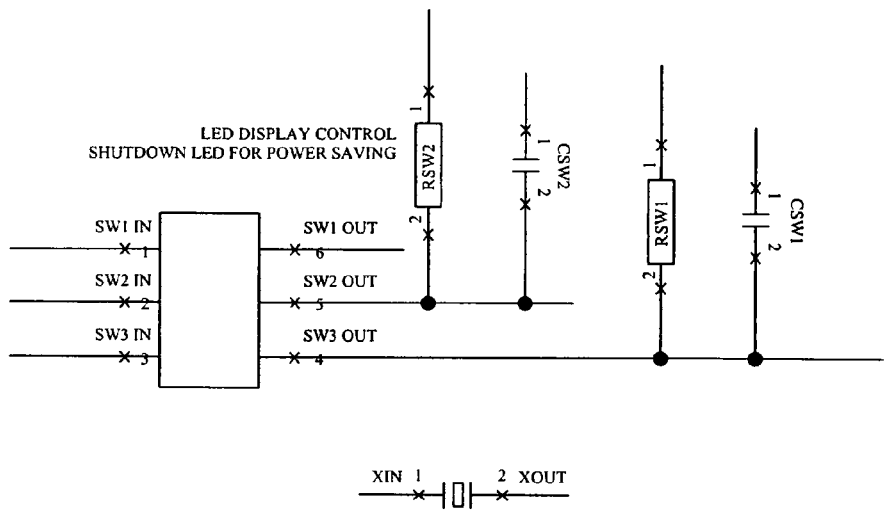
FIG. 14 is a wiring diagram of the switch in accordance with the first exemplary embodiment of the present invention.
Figure 15:
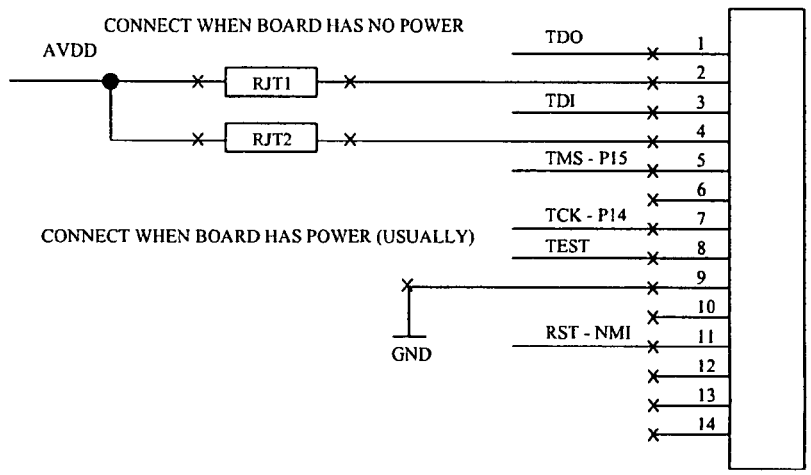
FIG. 15 is a wiring diagram of the JTAG interface with an output device in accordance with the first exemplary embodiment of the present invention.
Figure 16:
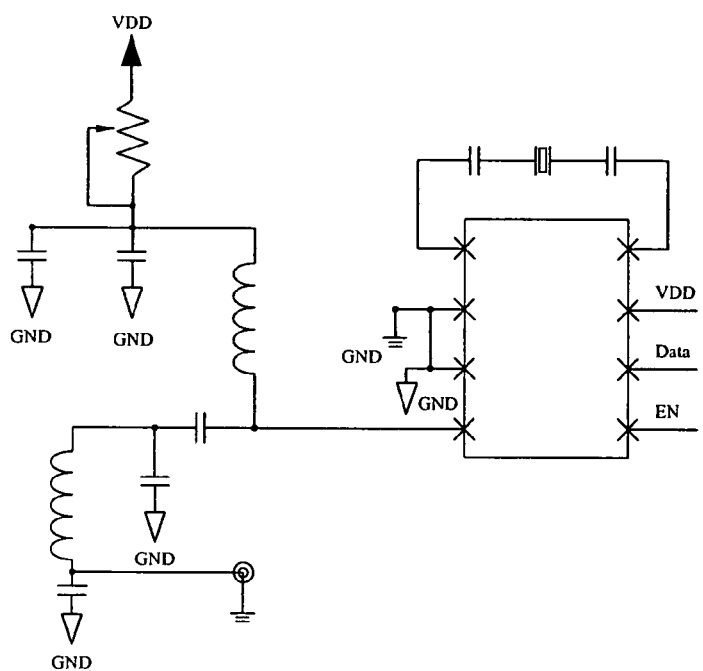
FIG. 16 is a wiring diagram of the ASK transmitter in accordance with the first exemplary embodiment of the present invention.
Figures 17, 18, 19:
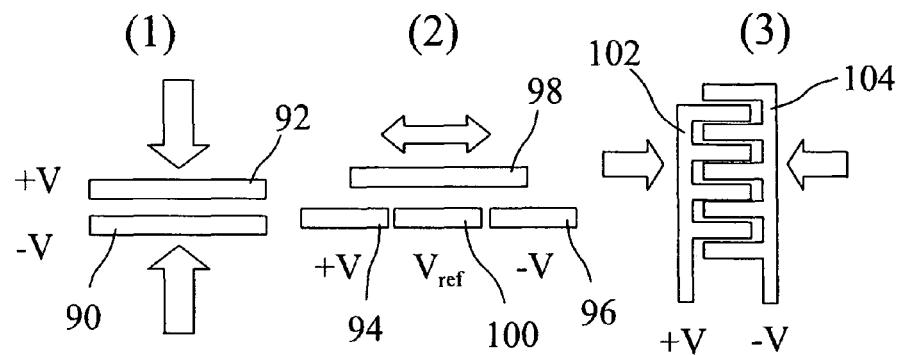
FIG. 17 is an exemplary orientational diagram representing a first exemplary capacitor structure incorporated into an exemplary sensor for use with the first exemplary embodiment of the present invention.
FIG. 18 is an exemplary orientational diagram representing a second exemplary capacitor structure incorporated into an exemplary sensor for use with the first exemplary embodiment of the present invention.
FIG. 19 is an exemplary orientational diagram representing a third exemplary capacitor structure incorporated into an exemplary sensor for use with the first exemplary embodiment of the present invention.

Referring to FIGS. 10-16, numerous exemplary wiring diagrams for various parts of the SOC and components of the remote receiver 91 are provided. For example, FIG. 10 is the wiring diagram for the display of the output signal for the remote receiver, while FIG. 11 is the wiring diagram of the interface switch to the transmitter of the SOC. FIG. 12 is the wiring diagram for the microcontroller, whereas FIG. 13 is the wiring diagram for the power supply circuit of the SOC. FIG. 14 is a wiring diagram to the switch of the output display for the remote receiver 91, while FIG. 15 is the interface circuit with the computer (acting as a remote receiver), and FIG. 16 is the wiring diagram for the ASK transmitter circuit of the SOC.

Referencing FIGS. 17-20, a first exemplary set of sensors (1), (2), (3) for use in the exemplary arrays 20, 36, 52 include interdigitated capacitor sensors fabricated from biocompatible materials. Pairs of electrodes are embedded in a polymer matrix to form capacitors that are responsive to deformation of the embedding material. More specifically, the capacitance of the capacitors changes as the spacing between the electrodes changes, which can be correlated to an exerted pressure resulting from changes in the configuration of the capacitor electrodes.

Figure 20:
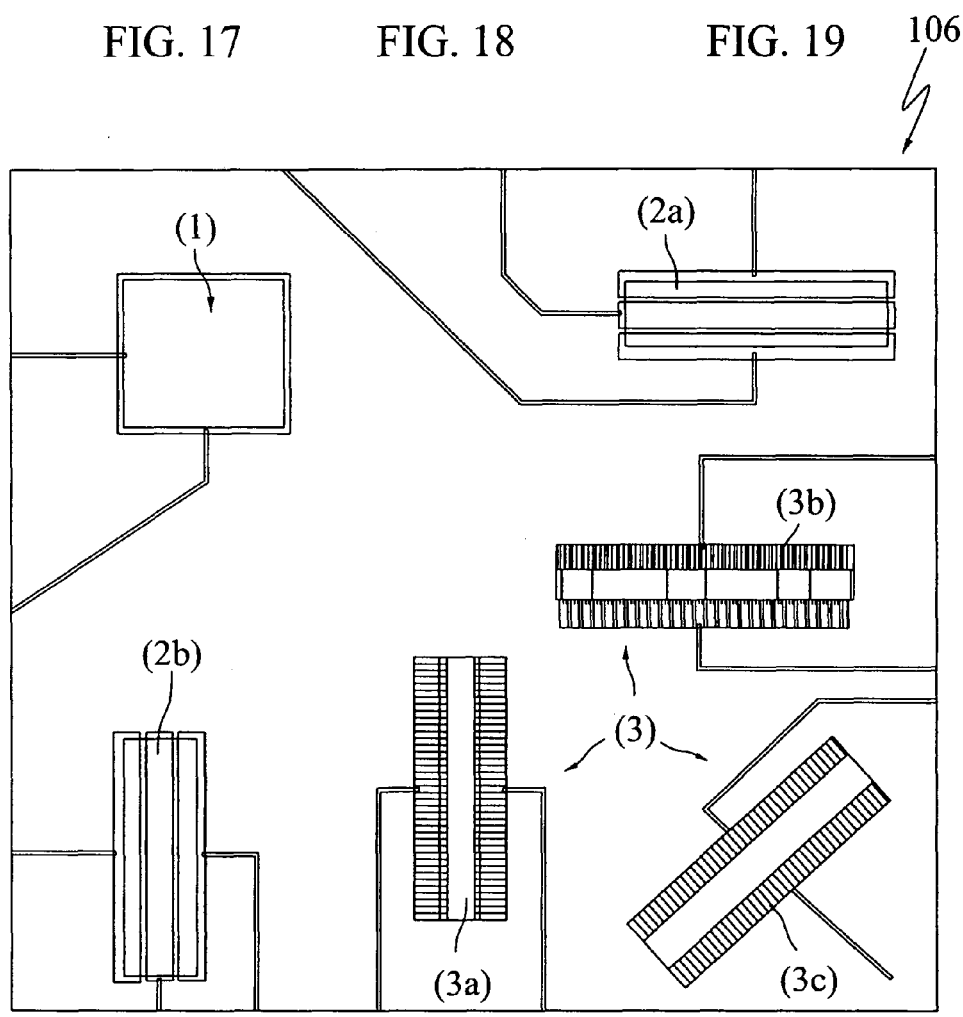
FIG. 20 is an exemplary orientational diagram representing load cell for use with the first exemplary embodiment of the present invention.

Referring to FIG. 20, a load cell 106 includes a compilation of the exemplary interdigitated capacitor sensors. The load cell 106 includes a first sensor (1) comprised of two capacitor plates 90, 92 separated from one another. The load cell 106 also includes two second sensors (2) comprised of a two-layer differential capacitor comprising two electrodes 94, 96 with a potential applied between them, an overlapping electrode 98 at a floating potential, and a fourth electrode 100 underneath the floating electrode serving as a testing potential. The load cell 106 also includes three third sensors (3) comprised of opposing capacitor plates with numerous fingers 102, 104.

Each of the sensors (1), (2), (3) is operative to measure a force from differing directions. A single first sensor (1) is operative to detect forces normal to the surface of the substrate. Dual second sensors (2) are arranged generally along the same plane, and also in the same plane as the first sensor (1), but are angled 90 degrees with respect to one another to detect shear in the plane orthogonal to the substrate. Finally, three third sensors (3) are also arranged in the same plane as the first and second sensors (1), (2), however, these sensors are angled 45 degrees with respect to one another and measure the in-plane strain. In sum, the load cell 106 provides an exemplary repeatable grouping of sensors in a single plane that are operative to detect exerted pressures in two dimensions of the plane, as well as in directions orthogonal to the plane to provide three dimensional mapping capabilities. An exemplary load cell 106 has dimension of 1 mm×1 mm, however, smaller dimensions are possible such as, without limitation, 0.1 mm×0.1 mm. An exemplar array 20, 36, 52 includes many multiples of load cells 106, such as two to eight hundred load cells 106.

Figure 21:
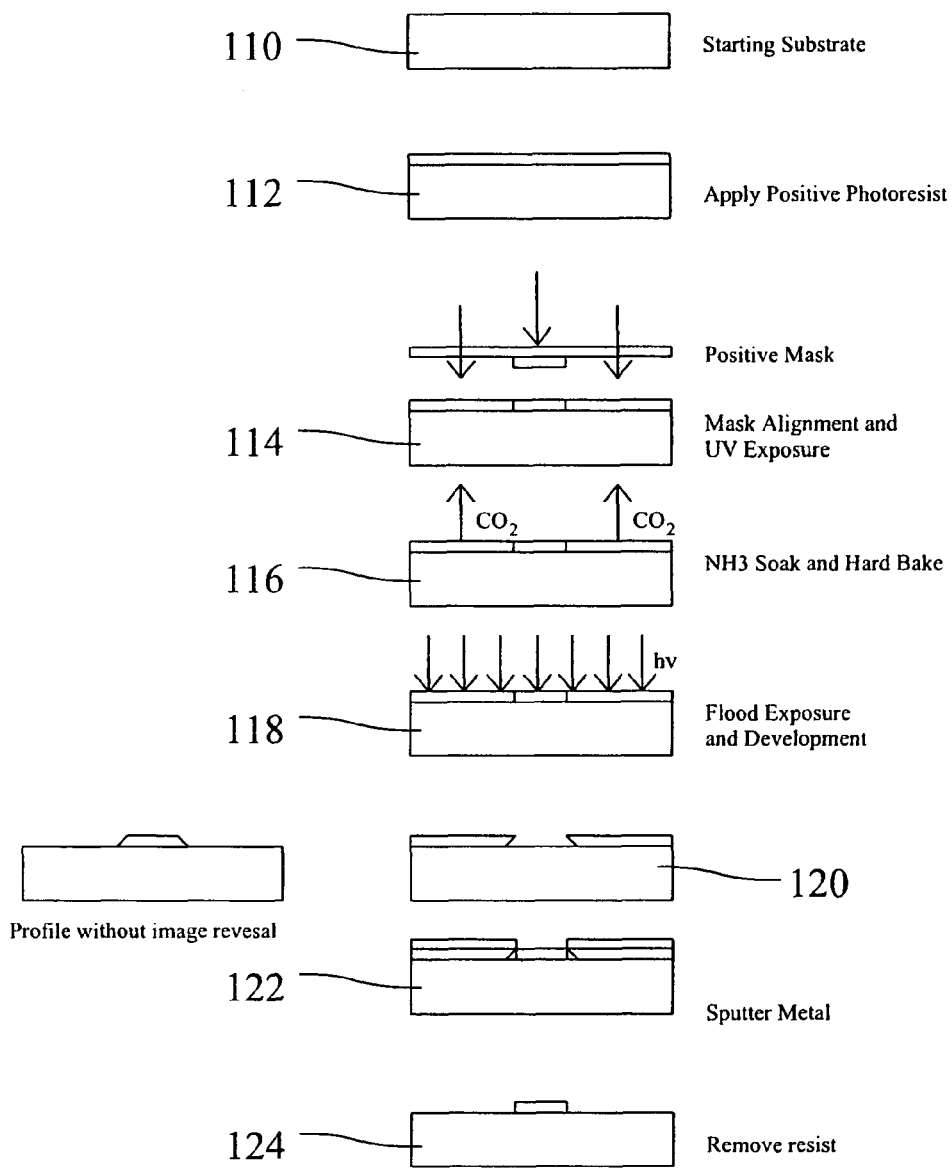
FIG. 21 is an exemplary process flow diagram for fabricating an exemplary sensor for use with the first exemplary embodiment of the present invention.

Referencing FIG. 21, fabrication of the first set of exemplary sensors includes utilization of MEMS fabrication techniques adapted from silicon-based microcontroller fabrication. In this exemplary embodiment, the first set of sensors may be either fabricated in an embedded state on the eventual prosthetic component, or may be fabricated remote from the eventual prosthetic component by as using a portable substrate structure such as medical-grade UHMW polyethylene, parylene films, or silicon wafers. Oxygen plasma reactive ion etching techniques may also be used as a surface pretreatment to enable the electrodes to adhere to certain substrate surfaces.

An initial procedure starts with obtaining a clean substrate surface at step 110, which in this exemplary process includes a silicon wafer, a polyethylene wafer, and a parylene film. The silicon wafer is cleaned using the piranha process, a 5:1 ratio of $H_2SO_4$ to $H_2O_2$ at 120 C. The polyethylene wafer is cleaned using a liquinox liquid soap cleaning solution with soft scrub, followed by an acetone rinse, a methanol rinse, and an isopropanol rinse. The surface of the polyethylene samples is then activated by exposure to an oxygen plasma or a combination of oxygen/nitrogen plasma. This step served to nano-roughen the surface and increase the energy of the surface by breaking down some of the polymer chains on the surface. The parylene substrate is oxidized with a 1 micron $SiO_2$ layer prior to applying 10 more microns of parylene.

After the substrates have been cleaned and prepared for photoresist deposition, step 112 comprises spin-coating each substrate with a Shipley S1818 photoresist at 3000 RPM for 30 seconds. Immediately subsequent to deposition of the photoresist, the substrates are soft-baked on a hot plate for 60 seconds at 90 C. Subsequent to the soft-baking step, contact lithography is used in step 114 to pattern transfer a positive mask onto the exposed surface of the substrates.

A baking step 116 follows the lithography step 114, where each substrate is baked for 80 minutes at 90 C in $NH_3$ gas in an image reversal oven. During the baking step 116, $NH_3$ gas diffuses into the exposed areas and neutralizes the byproducts of the photodecomposition process to render the exposed areas highly resistant to further change by exposure to light and insensitive to further developing.

Next, the substrates are subjected to a flood exposure step 118 for 60 seconds to render the areas adjacent to the neutralized areas soluble in the photoresist developer, thereby reversing the pattern originally exposed in the positive photoresist step 112. Each substrate is spray developed in a developer for 60 seconds, followed by a 30 second exposure to an oxygen plasma thereby ensuring that all of the photoresist is removed from the substrate in the developed areas, as shown by step 120.

Subsequently, a metal deposition step 122 includes evaporating 100 angstroms of titanium onto each substrate as an adhesion layer, followed by 1500 angstroms of gold comprising the bulk of the metal layer. In this exemplary process, the metal deposition step 122 covers the entire surface of the substrates, where the eventual structure is brought about by dissolving the photoresist in acetone or other photoresist solvent during the lift-off process, leaving metal only the desired areas. Each of the substrates is then cleaned in a polar solvent, such as methanol, resulting in the structure shown in step 124. Each subsequent layer of conductive material may be deposited by repeating the above recited process, interposing dielectric material between the conductive patterns. By way of example, and not limitation, an exemplary process might include a parylene dielectric coating step followed by photolithography patterning of vias and via etching in an oxygen plasma, and thereafter photolithographic masking and deposition of a subsequent electrode and trace layer. Those skilled in the art will understand the obvious alternatives drawn out by the aforementioned exemplary process.

Exemplary dimensions of the exemplary sensors (1), (2), (3) include, without limitation a 2 μm spacing between conductive plates having a thickness of approximately 2 μm, with length and widths depending upon the particular capacitive structure fabricated, which also may be said for the exemplary spacing and thickness dimensions recited.

Figures 22, 23:
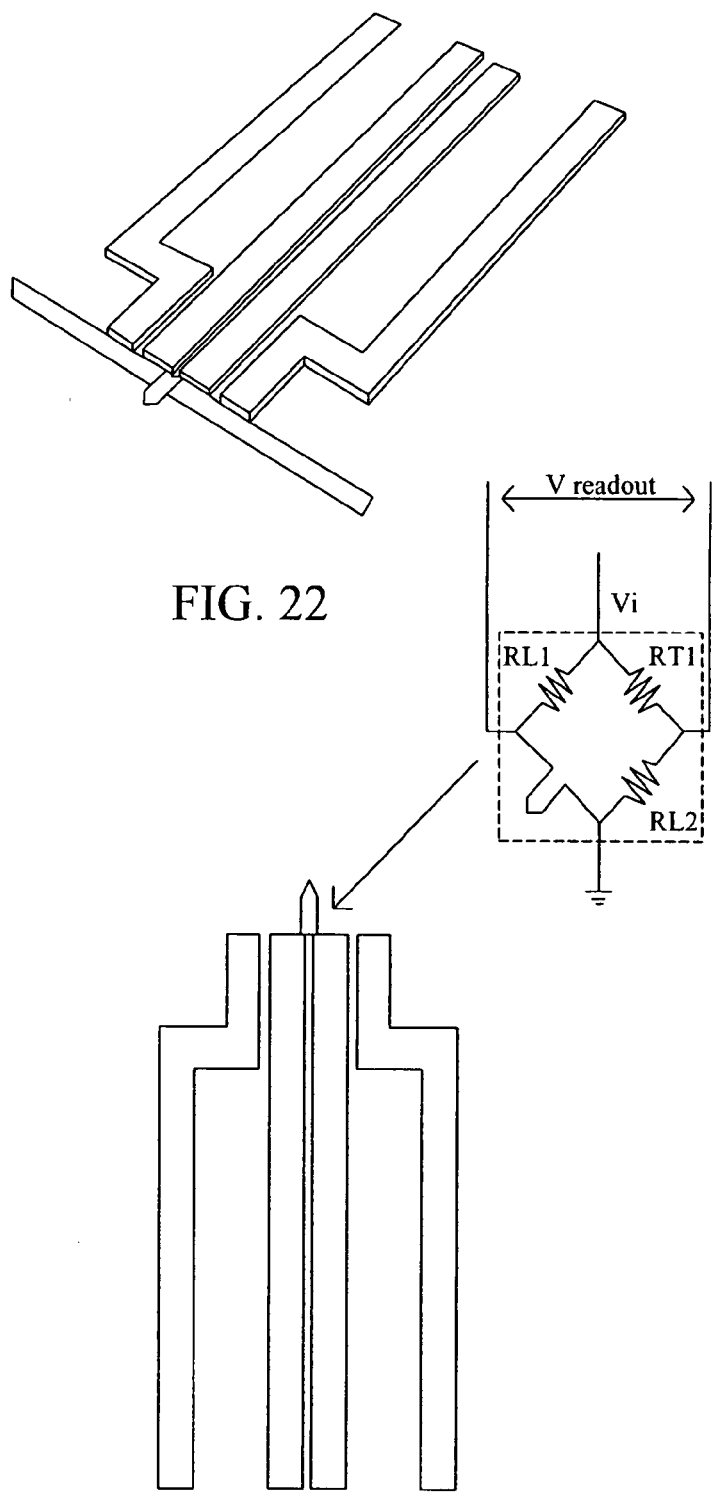
FIG. 22 is an elevated perspective view of an exemplary microcantilever sensor for use with the first exemplary embodiment of the present invention.
FIG. 23 is an overhead view of the exemplary microcantilever of FIG. 22 calling out the integrated Wheatstone bridge.
Figure 24:
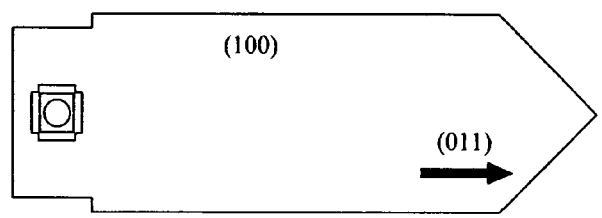
FIG. 24 is an overhead diagram of an exemplary cantilever with dimensions in μm.

Referring to FIGS. 22-24, a second set of exemplary sensors for use with the sensor arrays 20, 36, 52 of the present invention include sealed compartment sensors operative to measure in-vivo compartment pressures. The exemplary sensors comprise piezoelectric cantilevers fabricated from single crystal silicon, with each cantilever including an integrated Wheatstone bridge for automated offset balance. Piezoresistive microcantilevers include piezoresistive materials such as doped silicon that change in resistance according to the amount of strain imparted from the change in crystal structure. Hence, the relationship between the change in resistivity and the change in length (strain) can be characterized and calibrated as a strain sensor.

Multiple piezoelectric microcantilevers are mounted onto FR4 epoxy laminate in a predetermined pattern and embedded within an enclosure of epoxy material to form a portion or all of an exemplary array, which in exemplary form includes nine microcantilevers spaced from one another to evenly cover an area of 1 mm×1 mm. Each microcantilever includes a pyramidal tip located at the very end of the cantilever beam with a thickness of approximately 17 μm and dimensions as shown in FIG. 24. An epoxy, such as an FDA approved epoxy, is applied to the pattern of microcantilevers to form a pattern of capsules having a thickness of less than 2 mm. Each microcantilever is connected to an EMD 28, 38, 54 that multiplexes, signal conditions, amplifies and quantizes the signals. Those of ordinary skill will understand that certain tests, such as uniform compression tests, may be necessary to correlate the change in resistance to strain of the exemplary piezoelectric microcantilevers arrays.

Figure 25:
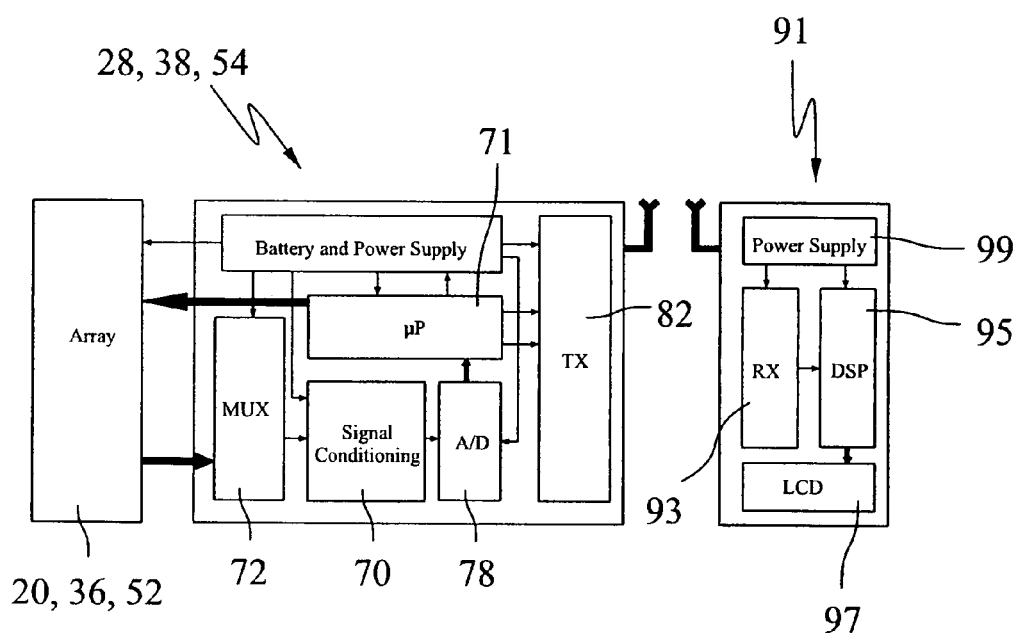
FIG. 25 is an exemplary schematic diagram showing the interaction between hardware components to sense conditions and generate data, manipulate the data, and transmit the data to a remote devices in accordance with the first exemplary embodiment of the present invention.

Referencing FIG. 25, each EMD 28, 38, 54 is designed to compensate and calibrate the imbalance in the Wheatstone bridge circuit due to the possible residual stress resulting from the epoxy encapsulation. A multiplexer 72 receives signals from the sensors of the array 20, 36, 52, where the multiplexed signals are conditioned by a signal conditioner 70, which transmits analog signals to a converter 78, thereby feeding digital signals to a microcontroller 71. The microcontroller 71 sends data signals to the transmitter 82, which ASK modulates the signals and disseminates the data in the form of radio frequency signals at 433.92 MHz. The EMD components are powered by an integral power source such as a battery, but may also be powered by electromagnetic induction or radio frequency (RF) induction. It is to be understood that the exemplary EMD structure of FIG. 25 may be utilized with other exemplary sensors and sensor arrays of the instant invention.

An exemplary remote receiver 91 includes a radio frequency receiver 93, a digital signal processor 95, and a display 97 for viewing the information derived from the wirelessly transmitted data. An on-board power supply 99 provides the necessary power to the components of the remote receiver, however, those of ordinary skill will understand that on-board power supplies may be replaced or supplemented by remote power supplies such as by way of power outlets. In exemplary form, the radio frequency signals are converted to electronic signals by the receiver 93 and output to the digital signal processor 95, which converts the signals into digital data that is output in an analog form to be viewed on the display 97, such as a liquid crystal display of a handheld device or computer monitor.

Figure 26:
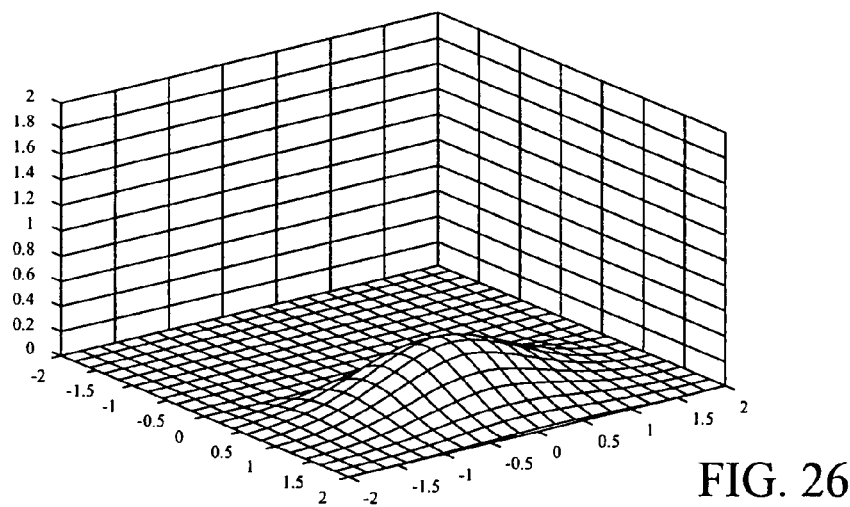
FIGS. 26-28 are graphical depictions from a visual display representing various degrees of a sensed condition, such as pressure or concentration of a chemical species.
Figure 27:
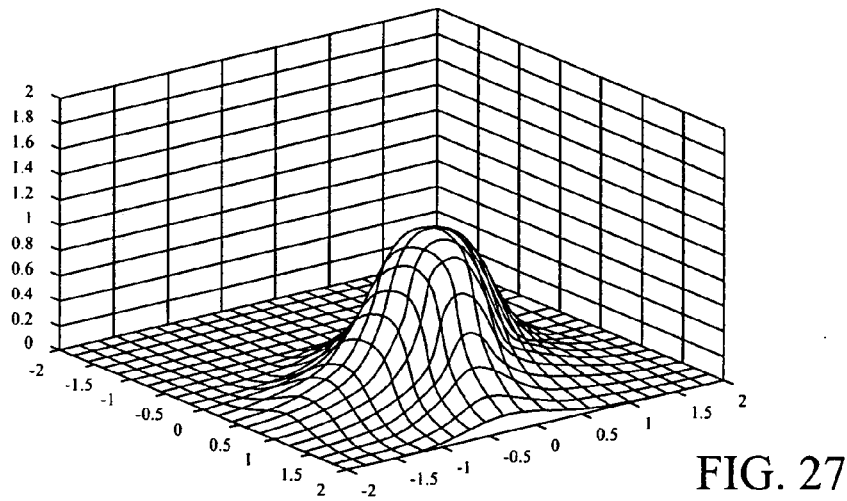
Figure 28:
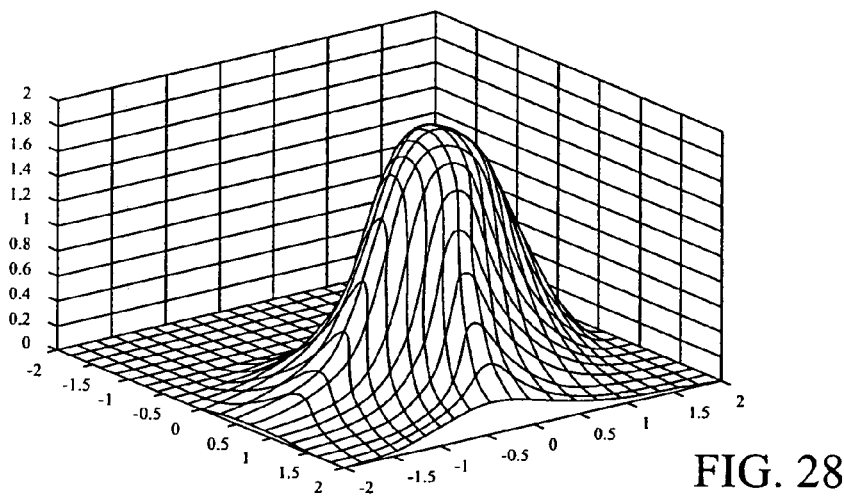

Referencing FIGS. 26-28, three exemplary data sets from a sensor array of the present invention are graphically depicted. In exemplary form, the graphical depictions reflect varying amounts of pressure detected by a certain sensor or groups of sensors of an array subsequent to implantation of the prosthesis. An exemplary graphical user interface includes a depiction of a three-dimensional model of the prosthesis (not shown), allowing a user to move a cursor over the model to gain feedback from a particular sensor or group of sensors regarding exerted pressures or a concentration of a particular substance or group of substances. In this manner, a surgeon or attending physician obtains substantially real-time feedback regarding the load distributions on the prosthesis, as well as feedback regarding the onset of infection or an insidious condition such as premature failure or improper biomechanical alignment.

Figure 29:
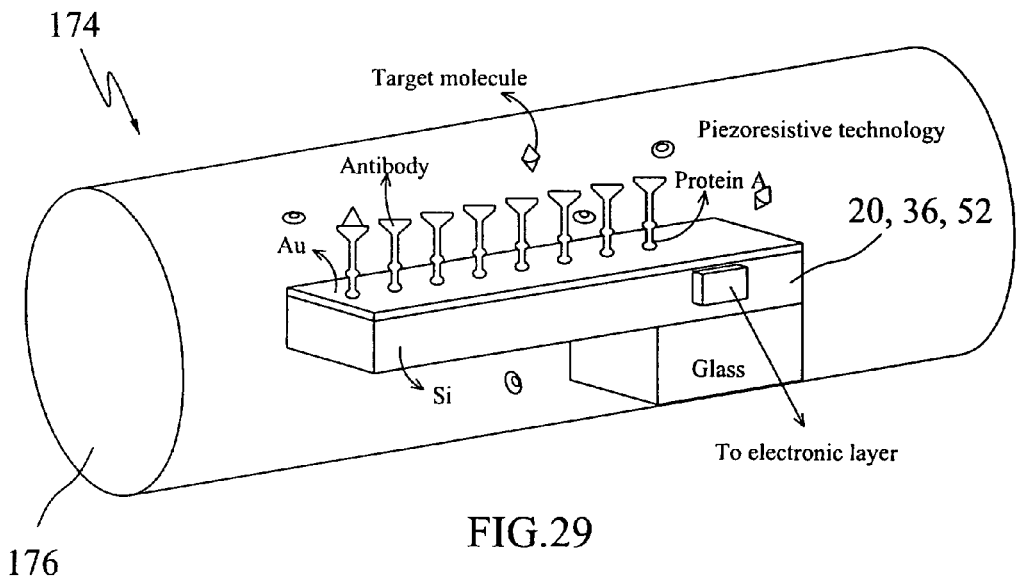
FIG. 29 is an exemplary piezoresistive microcantilever sensor mounted within a microchannel for sensing components, contaminants, and properties for use with the first exemplary embodiment of the present invention.
Figure 30:
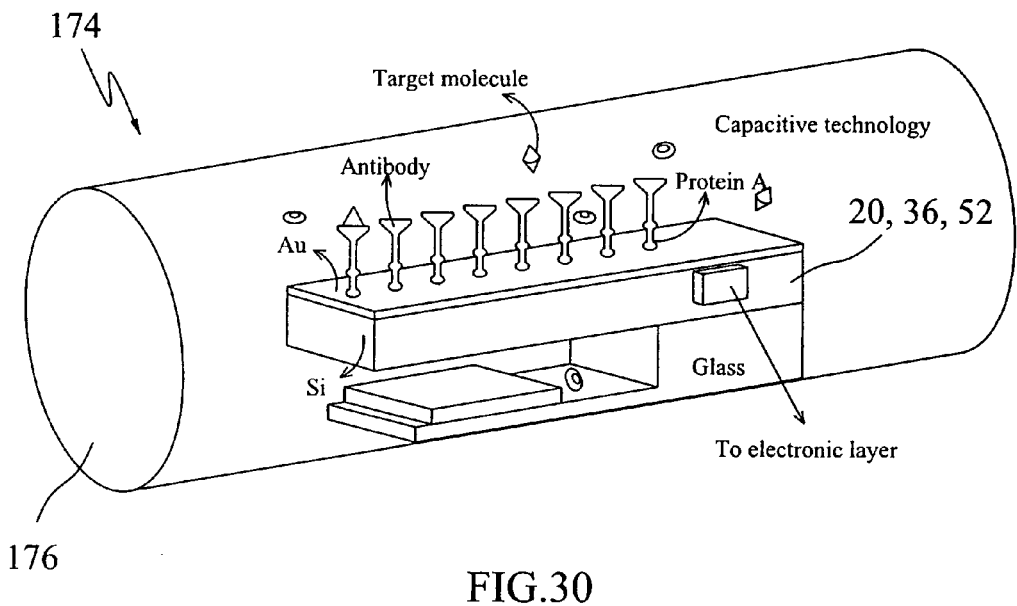
FIG. 30 is an exemplary capacitive microcantilever sensor mounted within a microchannel for sensing components, contaminants, and properties for use with the first exemplary embodiment of the present invention.
Figure 31:
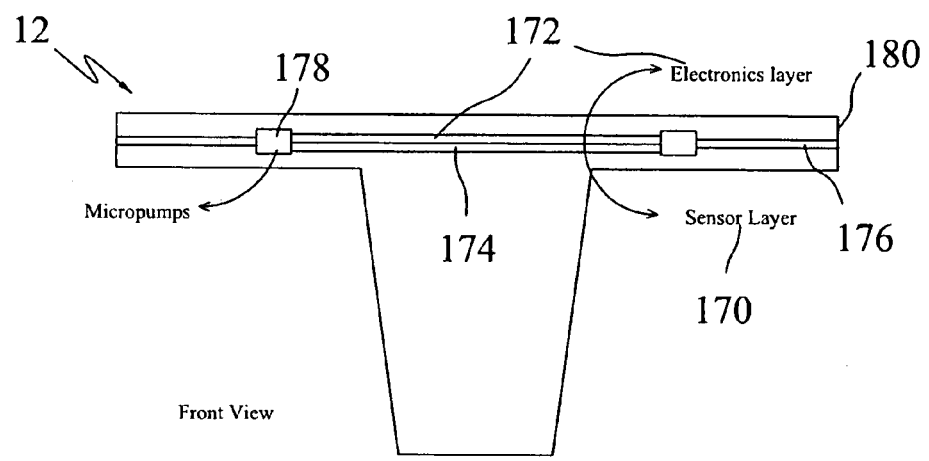
FIG. 31 is an exemplary tibial tray housing a dual-layer structure for use with the exemplary capacitive or piezoresistive microcantilevers of the present invention.
Figure 32:
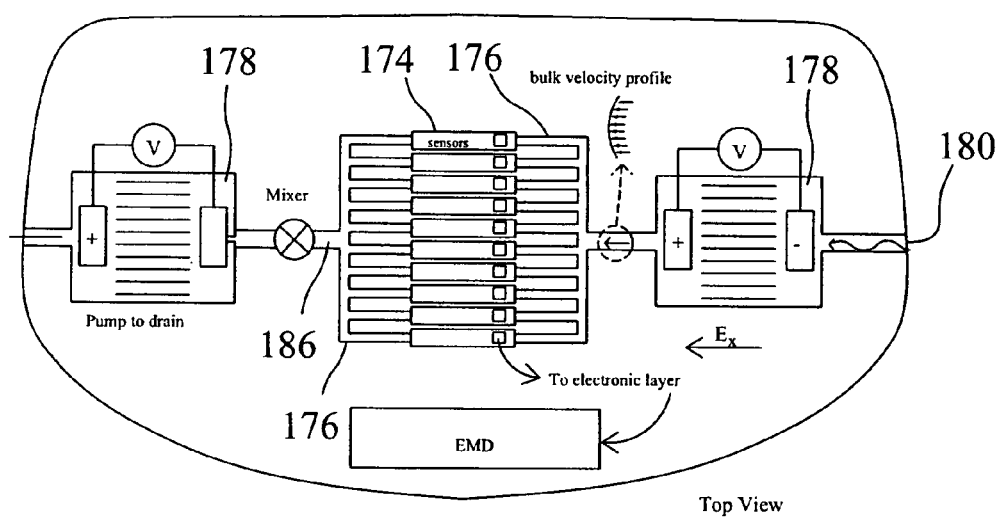
FIG. 32 is an overhead, exposed view of the tibial tray of FIG. 31 showing the exemplary layout of the capacitive or piezoresistive microcantilevers of the present invention, as well as the micropumps feeding fluid into the microchannels and discharging fluid from the microchannels.
Figure 33:
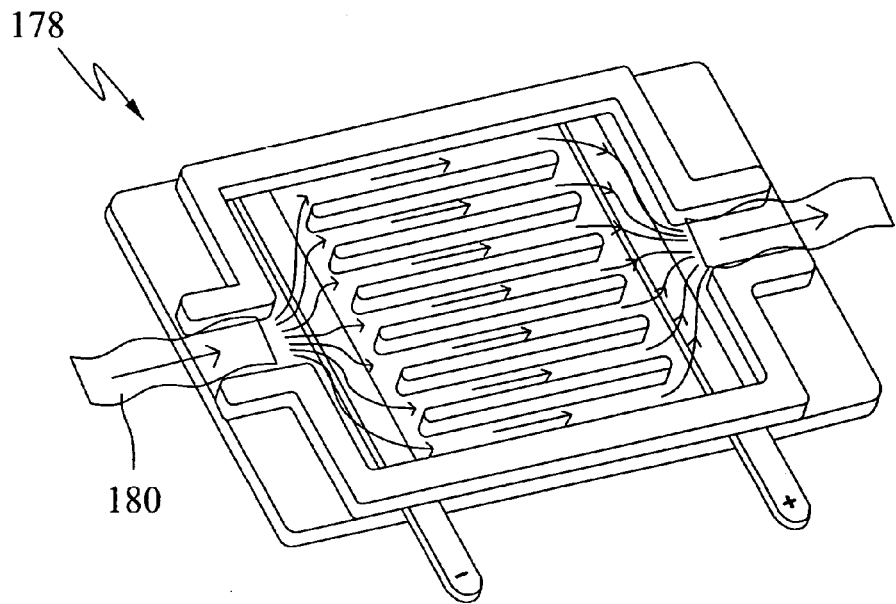
FIG. 33 is an exposed view of a micropump in accordance with the present invention showing how fluid flows through the pump as an electric potential is applied at the terminals.

Referring to FIGS. 29 and 30, a third set of exemplary sensors for use with the sensor arrays 20, 36, 52 of the present invention include microchannels lined with MEMS microcantilever sensors 174 (resistive, FIG. 29, or capacitive, FIG. 30) to measure fluid properties and contaminations. These sensors are operative to detect certain components, contaminants, and properties relevant to the prosthetic joint and generate detection data representative of the component, contaminant, or property detected. Exemplary microcantilevers may be fabricated consistent with the disclosures of U.S. Pat. Nos. 6,289,717, 5,719,324, and 6,763,705, the disclosures of each of which are hereby incorporated by reference.

The following is a nonexhaustive, exemplary listing of the components, contaminants, and properties that may be detected in the synovial fluid that bathes the prosthetic joint. It is to be understood that the exemplary sensors for use with the present invention may detect or measure one or more of the following: viscosity of the synovial fluid; pH of the synovial fluid; cell count within the synovial fluid; protein within the synovial fluid; phospholipids within the synovial fluid; hyaluronic acid within the synovial fluid; leukocytes within the synovial fluid; neutrophils within the synovial fluid; bacterial deoxyribonucleic acid within the synovial fluid; antibodies within the synovial fluid; glucose concentration within the synovial fluid; lactate dehydrogenase (LDH) within the synovial fluid; uric acid crystals within the synovial fluid; MMP-9 antigens (gelatinase-B) within the synovial fluid; nerve growth factor within the synovial fluid; excitatory amino acids (EAA) glutamate and aspartate within the synovial fluid; insulin-like growth factor I (IGF-I) and its binding proteins (IGFBP) 3 and 4 within the synovial fluid; oxidase activity within the synovial fluid; polyamine oxidases within the synovial fluid; caeruloplasmin (Cp) concentration within the synovial fluid; beta-glucuronidase content within the synovial fluid; S100A8/A9 within the synovial fluid; C reactive protein within the synovial fluid; rheumatoid factor within the synovial fluid; C3 and C4 within the synovial fluid; metal particulate within the synovial fluid; polyethylene particulate within the synovial fluid; bone particulate within the synovial fluid; cement particulate within the synovial fluid; osteolytic enzymes within the synovial fluid; genetic markers within the synovial fluid; antibody markers within the synovial fluid; temperature of the synovial fluid; specific gravity of the synovial fluid; and white cells (and differential cell type) within the synovial fluid.

Referring to FIGS. 31-34, the third set of exemplary sensors may be incorporated into a dual-layer design adapted to be embedded within one or more of the prosthetic implants 12, 14, 16. In this exemplary dual-layer structure, a first layer is comprised of a sensor layer 170 and a second layer is comprised of an electronics layer 172. The sensor layer 170 includes a plurality of functionalized microcantilevers 174, microfluidic channels 176, and micropumps 178. A small inlet 180 to the microfluidic channel corresponds with an opening through the prosthetic implant 12, 14, 16 (for example, the tibial tray 12) to allow interstitial fluids to contact the sensor layer 170 of the array. The microfluidic channels 176 are in communication with the micropumps 178, which are operative to pump a fixed volume of interstitial fluid into contact with the microcantilevers 174 to allow generation of chemical analysis data representative of the constituency of the interstitial fluid exposed to the microcantilevers 174. A downstream portion 186 of the microfluidic channels 176 combines the individual fluid paths, subsequent to passing beyond the microcantilevers 174, into a single outlet stream that is removed by the action of a second micropump 178. Exemplary micropumps 178 include, without limitation, micropumps transporting fixed volumes of fluid under the influence of an electric field such as those disclosed in U.S. Pat. No. 6,733,244, the disclosure of which is incorporated by reference (see FIG. 33), as well as Alzet microosmotic pumps available from Durect Corporation (www.alzet.com).

Figure 34:
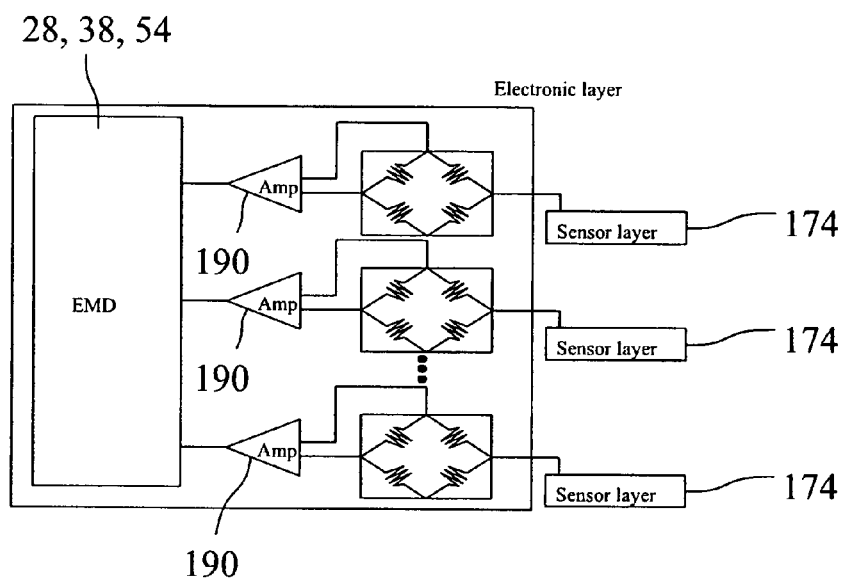
FIG. 34 is a schematic diagram showing the electrical connection between the sensors and control circuitry for use with the present invention.
Figure 35:
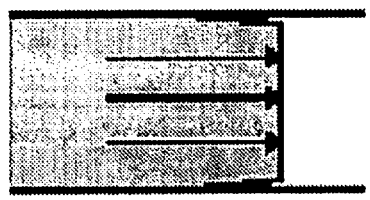
FIG. 35 is a schematic view of the phenomenon of electro-osmotic flow and the equation governing the flow transport.
Figure 36:
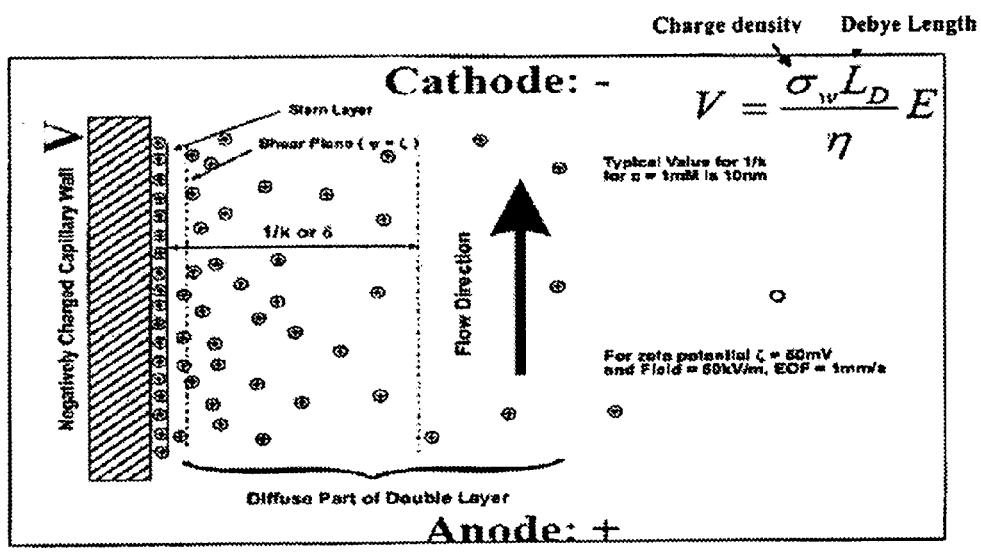
FIG. 36 is a schematic view of the effect of an electrical double layer on fluid flow.

Referencing FIG. 34, each sensor array 20, 36, 52 is in communication with an EMD (see FIG. 25) to receive deflection signals representative of the deflection of the functionalized microcantilevers 174. An amplifier 190 may interpose the microcantilevers 174 and EMD 28, 38, 54 to amplify the deflection signals of the functionalized microcantilevers 174.

A complementary pair of microcantilevers 174 may be utilized, one reference set corresponding to a controlled environment without any bound biochemical agents, while a second signal set, identical to the first set, is exposed to biochemical agents within the interstitial fluid. External vibrations cause both the signal and the reference cantilever set to vibrate and without the reference set, such vibrations might, in severe conditions, overwhelm the minute deflection forces resulting from the binding of biochemical agents to the microcantilevers 174. Subtracting the reference vibrations from the signal vibrations helps reduce this interference.

The output signal from each piezoresistive microcantilever 174 is measured using an on-chip Wheatstone bridge. One of the cantilevers then acts as a mechanical filter for the noise that both the measuring cantilever and the reference cantilever experience using the following expression:

$$\frac{V_0}{V_{bias}} = \frac{1}{4}\frac{\Delta R}{R}$$

The fractional change in resistance ($\Delta R/R$) of a piezoresistive cantilever is described by the following expression:

$$\frac{\Delta R}{R} = \beta \frac{3\pi_L(1-\upsilon)}{t}(\sigma_1 - \sigma_2) \quad \text{Equation (1)}$$

Where $\pi_L$ is the piezoresistive coefficient of silicon along the axis, $\sigma1$ is the longitudinal stress, $\sigma2$ is the transverse stress, t is thickness of cantilever, $\nu$ is Poisson's ratio, and $\beta$ is a factor that adjusts for the thickness of the piezoresistor. From Equation (1), the ratio ($\Delta R/R$) is proportional to differential stress ($\sigma1-\sigma2$). Differential stress distribution over a cantilever surface depends on the geometric factors of the layers and the chemo-mechanical forces between the biomolecules and the capture or hybridization layers. Therefore, the deflection signal can be increased by maximizing differential stress ($\sigma1-\sigma2$) by changing the geometric factors.

The change in resistance of a piezoresistive cantilever is related to the analyte and receptor concentration by the following expression:

$$\Delta\sigma = (\Delta\sigma_0)\left[1 - e^{-k_f C_\infty N_r t}\right] \quad \text{Equation (2)}$$

$$\frac{\Delta R}{R} = \Pi[(\Delta\sigma_1)_0 - (\Delta\sigma_2)_0]\left[1 - e^{-k_f C_\infty N_r t}\right] \quad \text{Equation (3)}$$

Where

Effective reaction rate $K_f=(K-a|u|)$, u=flow velocity;

$\Pi=\beta*3\pi_L(1-\nu)/t$ is the piezoresistor coefficient, $(\Delta\sigma1)_0=\Delta G_1 N_0 A^{-1}{}_m A^{-1}$, $(\Delta\sigma2)_0=\Delta G_2 N_0 A^{-1}{}_m A^{-1}$, $\Delta G$=change in the Gibbs free energy caused by the adsorption process;

$N_r$=Number of available receptors;

$C\infty$=analyte concentration;

$A_m$=area of receptor coating; and

A=number of analyte molecules per mole.

Also, the deflection (z) of the tip of an ordinary microcantilever is calculated from using Stoney's Equation:

$$z = \frac{3\ell^2(1-\upsilon)}{Et_m^2}\Delta\sigma \quad \text{Equation (4)}$$

where $\lambda$, $\nu$, E, $\Delta\sigma$, and $t_m$ are the microcantilever's effective length, Poisson's ratio, Young's modulus, differential surface stress and its thickness. Using Equations (2) and (4), the deflection of the cantilever due to surface stresses is measured.

From Equations (2), (3), & (4), it is clear that in order to measure the change in resistance, one needs to know the analyte concentration and the number of available receptors and the flow velocity of the fluid.

As the characteristic dimensions of the channels decrease to micro ranges, the fluid flow behaviors are increasingly influenced by interfacial effects such as the electrical double layer (EDL). Because of the EDL influence, the microchannel flows deviate from predications of the traditional Navier-Stokes equations. The large surface-area-to-volume ratio in the microchannel causes the excess shear stress effect of the flow.

To consider EDL and electrostatic field effects on fluid flow through the microchannel, the distribution of electrical potential and net charge density between the two plates must be evaluated. Consider a liquid phase containing positive and negative ions in contact with a planar negatively charged surface. An EDL field will be established. According to the theory of electrostatics, the relationship between the electrical potential and the net charge density per unit volume $\rho_e$ at any point in the solution is described by the two-dimensional Poisson equation $$\frac{\partial^2 \psi}{\partial x^2} + \frac{\partial^2 \psi}{\partial y^2} = -\frac{\rho_e}{\varepsilon\varepsilon_0}, \quad \text{Equation 5}$$

Where $\rho_e$ is the charge density, $\in$ is the dielectric constant of the medium, and $\in_0$ is permittivity of vacuum. For any fluid consisting of two kinds of ions of equal and opposite charge ($Z^+$ and $Z^-$), the number of ions of each type is given by the Boltzmann equation $$n^-=n_0 e^{ze\psi/k_b T}, n^+=n_0 e^{-ze\psi/k_b T}, \quad \text{Equation 6}$$

where $n^+$ and $n^-$ are the concentrations of the positive and negative ions, $n_0$ is bulk concentration of ions, $e^{ze\psi/k_b T}$ is the Boltzmann factor, $k_b$ is the Boltzmann constant, and T is the absolute temperature. The local net charge density in a unit volume of the fluid is given by $$\rho_e=(n^+-n^-)ze=-2n_0 ze \sin h(ze\psi/k_b T). \quad \text{Equation 7}$$

Substituting Equation 7 into Equation 5, we obtain a nonlinear two dimensional Poisson-Boltzmann equation, $$\frac{\partial^2 \psi}{\partial x^2} + \frac{\partial^2 \psi}{\partial y^2} = \frac{2nze}{\varepsilon\varepsilon_0}\sinh(ze\psi/k_b T).$$

Microchannel flow is changed by the presence of an electrostatic potential field. For the current study of electro-osmotic flow, it is assumed that the applied electrostatic potential is much larger than the streaming potential induced by the current due to transport of charges by the liquid flow. Therefore, we obtain the distribution of the electrostatic field by solving the Laplace equation:

$$\frac{\partial^2 \phi}{\partial x^2} + \frac{\partial^2 \phi}{\partial y^2} = 0.$$

The Navier-Stokes equations mathematically represent the fluid flow in general cases. However, they have to be modified for the case of microchannel flow to include the electrical force generated by the interaction between EDL and the electrical potential field. The equations of motion for an incompressible liquid are given by $$\nabla \cdot \overline{u} = 0$$

$$\frac{\partial \overline{u}}{\partial t} + \overline{u} \cdot \nabla \overline{u} = -\frac{1}{\rho_f} \nabla p + \frac{\mu}{\rho_f} \nabla^2 \overline{u} - \frac{\rho_e}{\rho_f}(\nabla(\psi + \phi))$$

In this equation, $\overline{u}$ is the velocity vector containing u and v components along the x and y directions, $\rho_f$ and $\mu$ are the density and dynamic viscosity of the liquid, respectively, and $\rho_e$ is the charge density.

The channel length is assumed to be long enough that the flow is fully developed at the outflow boundary. Initially, liquid fluid is fills the channel and the flow is stationary. An equilibrium electrical double layer is formed near wall boundaries. Once the driving force (the static electrical potential at the inlet) is activated, the flow starts to move. No slip velocity boundary conditions are used at the walls. At the flow inlet, the zero velocity gradient is assumed because the mass flow rate is determined by the activated electrical potential.

The boundary conditions applied for this case are:

$$X = 0 \quad \frac{\partial u}{\partial x} = 0, \quad \frac{\partial v}{\partial x} = 0, \quad \frac{\partial p}{\partial x} = 0, \quad \frac{\partial \psi}{\partial x} = 0, \quad \phi = C_1$$

$$X = L \quad \frac{\partial u}{\partial x} = 0, \quad \frac{\partial v}{\partial x} = 0,$$

$$p(L, y) = \int_0^y Gx \cdot \sinh\psi \frac{\partial \psi}{\partial y} dy, \quad \frac{\partial \psi}{\partial x} = 0, \phi = C_2$$

$$Y = 0 \quad u = 0, \quad v = 0, \quad \frac{\partial p}{\partial y} = \frac{1}{Re}\frac{\partial^2 v}{\partial y^2} + Gx \cdot \sinh\psi \frac{\partial \psi}{\partial y},$$

$$\psi = C_3, \frac{\partial \phi}{\partial y} = 0$$

$$Y = W \quad u = 0, \quad v = 0, \quad \frac{\partial p}{\partial y} = \frac{1}{Re}\frac{\partial^2 v}{\partial y^2} + Gx \cdot \sinh\psi \frac{\partial \psi}{\partial y},$$

$$\psi = C_4, \frac{\partial \phi}{\partial v} = 0,$$

where C1, C2, C3, and C4 are known constants.

The micropump transports fluid onto the sensor array through a parallel microchannel structure as shown in FIG. 34. The functionalized microcantilevers within the microconduits are deflected by predetermined compositions, thereby operating to provide a predetermined chemical analysis of the fluid.

The design of the force-sensing prosthetic joint components using wireless sensor and telemetry technology is a major advancement for the orthopaedic and CAOS industries. An exemplary sensor array includes numerous sensors oriented in a triangular fashion to measure lateral and medial condylar reaction forces, total reaction forces, and the difference in reaction forces between medial and lateral aspects of the permanent or trial prosthetic component. The sensors include a capacitive readout and power for the telemetry is provided inductively. The power can be supplied either by a coil worn near the knee during testing or a small rechargeable battery is incorporated into this system so that the rechargeable battery is charged inductively prior to testing. Alternatively, a piezoelectric sensor providing an output charge may be utilized to power the system dependent upon the dynamic load available to the sensor. This charge in certain instances is sufficient power the telemetry system and recharge any electrical components used for the telemetry system.

The present invention may be utilized to correct ligament balancing in the knee joint during the time of surgery utilizing readings gathered from trial and permanent prosthetic components. In addition, utilizing the present invention to measure the loads, to measure the symmetry of the loads at the femorotibial interface in a knee replacement, and to measure the composition of the synovial fluid intra-operatively allows a physician to greatly enhance ligament balancing and inhibiting premature wear of the prosthetic. The present invention may also be utilized to detect bearing surface forces that, in turn, may be used to determine active muscle forces, such as the quadriceps muscle, and/or resistive force, such as ligament forces that provide constraint to the knee joint.

For example, if abnormal polyethylene levels are detected and the loading conditions within the joint are known it might be possible to correct the imbalances and reverse or decrease wear. If metal debris is detected, wear-through of the insert or excessive corrosion or wear from the Morse taper junctions in modular implants is detected, an appropriate intervention may be performed.

It is also within the scope of the invention that the sensors and control electronics be incorporated into other prosthetic components including, without limitation, femoral cup prostheses, femoral cup insert prosthesis, femoral stem prosthesis, and other joint replacement components. Those of ordinary skill will readily understand how to adapt the exemplary teachings recited herein to fabricate and use variations such as those discussed above. Moreover, the exemplary teachings of the instant invention are likewise applicable to prosthetic trail components in order to at least sense pressure to facilitate proper biomechanical operation of the prosthetic joint once implanted. Moreover the exemplary teachings are applicable to fixed bearing and mobile bearing prosthetic implants.

It is also within the scope of the invention that the microsensors and control electronics are incorporated into prosthetic braces to gauge pressures exerted against the brace as a manner to evaluate the effectiveness of the brace and whether the mammalian body part being braced is becoming stronger and/or whether the force distribution against the brace is within predetermined tolerances, tending to show proper biomechanical function.

It is further within the scope of the instant invention that the sensors and control electronics are responsive in nature in order to automatically prompt the recipient of the prosthesis that one or more monitored conditions is outside of the predetermined range, thereby requiring consultation with the surgeon or attending physician. By way of example, and not limitation, the prosthetic joint may incorporate a wobble insert that would be activated and thereby vibrate when one of more monitored conditions is outside of the normal parameters. Other exemplary methods of actively communicating with the recipient include direct communication to a remove device 91 given to the recipient that would self-diagnose the condition and request the patient to consult the surgeon or attending physician.

For purposes of the instant invention, microchannel includes those conduits having diameters or restrictive dimensions of 0.1 mm or less, and microsensors include those sensors having dominant dimensions generally less than 1000 μm, and certainly those having dominant dimensions less than 100 μm.

Following from the above description and invention summaries, it should be apparent to those of ordinary skill in the art that, while the subject matter described herein constitutes exemplary teachings of the present invention, the invention contained herein is not limited to these precise teachings and changes may be made to the aforementioned teachings without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any one of the claims, since the invention is defined by the claims and since inherent and/or unforeseen advantages of the present invention may exist even though they may not have been explicitly discussed herein.

What is claimed is:

1. A prosthetic device for implantation into a mammalian body having a bodily fluid, the prosthetic device prosthesis comprising:
   a prosthesis having at least one articular surface adapted to form a joint with one of a bone and a second prosthetic implant, the one of the bone and the second prosthetic implant applying a load to the articular surface of the prosthesis after implantation of the prosthesis into the mammalian body, the prosthesis for being bathed by the bodily fluid when implanted in the mammalian body, the prosthesis including a microchannel and a micropump in fluid communication with the microchannel to pump the bodily fluid through the microchannel,
   a sensor array comprising a plurality of sensors mounted to the prosthesis; and
   an electronics structure for receiving signals from the sensor array and wirelessly transmitting representative signals to a remote receiver;
   wherein at least one of the plurality of sensors is operative to sense pressure, applied to the at least one articular surface of the prosthesis at the joint, in at least two axes generally perpendicular to one another, and
   wherein at least one sensor of the plurality of sensors is in fluid communication with the microchannel.

2. The prosthetic device of claim 1, wherein the electronics structure includes a timing circuit configured to automatically activate the sensor array and to automatically deactivate the sensor array.

3. The prosthetic device of claim 1, wherein the plurality of sensors include at least one of resistive microcantilevers, piezoelectric microcantilevers, and microcapacitor sensors.

4. The prosthetic device of claim 1, wherein the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trial hip replacement acetabular cup insert prosthesis.

5. The prosthetic device of claim 1, wherein the electronics structure includes a microcontroller, an amplifier, and a transmitter, the microcontroller being operatively coupled to the amplifier to amplify the signals from the sensor array and being operatively coupled to the transmitter to transmit amplified signals to the remote receiver, the remote receiver being located outside the mammalian body.

6. The prosthetic device of claim 1, wherein the electronics structure includes an application specific integrated circuit, which includes a filter for filtering out low frequency noise.

7. The prosthetic device of claim 1, wherein the electronics structure includes an application specific integrated circuit, which includes a multiplexer for multiplexing signals from the sensor array.

8. The prosthetic device of claim 1, wherein the electronics structure includes an application specific integrated circuit, which includes an analog-to-digital converter for converting analog signals from the sensor array to digital signals.

9. The prosthetic device of claim 1, wherein the electronics structure includes an application specific integrated circuit, which includes a processor for processing signals from the sensor array.

10. The prosthetic device of claim 1, wherein at least one of the plurality of sensors is operative to sense temperature.

11. The prosthetic device of claim 1, wherein the at least one of the plurality of sensors operative to sense pressure applied to the prosthesis comprise a first sensor of a first type selected from an interdigitated capacitor, a capacitor having parallel plates and sensing forces perpendicular to the plates, and a differential capacitor sensing shear forces.

12. The prosthetic device of claim 11, further comprising a second sensor of a second type selected from the interdigitated capacitor, the capacitor having parallel plates and sensing forces perpendicular to the plates, and the differential capacitor sensing shear forces, the second type being different than the first type.

13. The prosthetic device of claim 12, wherein the first sensor and the second sensor are in a plane.

14. The prosthetic device of claim 1, wherein the at least one sensor of the plurality of sensors operative to sense pressure in at least two axes include a first sensor sensing pressure in a first axis and a second sensor sensing pressure in a second axis which is angled relative to the first axis.

15. The prosthetic device of claim 1, wherein the at least one sensor of the plurality of sensors in fluid communication with the microchannel comprises a microcantilever sensor detecting at least one of a predetermined component of the bodily fluid in the microchannel, a predetermined contaminant of the bodily fluid in the microchannel, and a predetermined property of the bodily fluid in the microchannel.

16. A prosthetic device for implantation into a mammalian body having bodily fluid, the prosthetic device comprising:
    a prosthesis having at least one articular surface adapted to form a joint with one of a bone and a second prosthetic implant, the one of the bone and the second prosthetic implant applying a load to the articular surface of the prosthesis after implantation of the prosthesis into the mammalian body, the prosthesis for being bathed by the bodily fluid when implanted in the mammalian body, the prosthesis including a microchannel and a micropump in communication with the microchannel to pump the bodily fluid through the microchannel;
    a sensor array comprising a plurality of sensors mounted to the prosthesis; and
    an electronics structure for receiving signals from the sensor array and wirelessly transmitting representative signals to a remote receiver;
    wherein at least one of the plurality of sensors is operative to sense pressure, applied to the at least one articular surface of the prosthesis at the joint, in at least two axes generally perpendicular to one another.

17. The prosthetic device of claim 16, wherein the electronics structure includes a timing circuit configured to automatically activate the sensor array and to automatically deactivate the sensor array.

18. The prosthetic device of claim 16, wherein the plurality of sensors includes at least one of resistive microcantilevers, piezoelectric microcantilevers, and microcapacitor sensors.

19. The prosthetic device of claim 16, wherein the prosthesis includes at least one of a knee replacement femoral prosthesis, a knee replacement tibial prosthesis, a knee replacement tibial tray prosthesis, a hip replacement femoral prosthesis, a hip replacement acetabular cup prosthesis, a hip replacement acetabular cup insert prosthesis, a trial knee replacement femoral prosthesis, a trial knee replacement tibial prosthesis, a trial knee replacement tibial tray prosthesis, a trial hip replacement femoral prosthesis, a trial hip replacement acetabular cup prosthesis, and a trial hip replacement acetabular cup insert prosthesis.

20. The prosthetic device of claim 16, wherein at least one sensor of the plurality of sensors of the sensor array is operative to sense at least one of: leukocyte concentration, neutrophil concentration, bacterial deoxyribonucleic acid concentration, antibody concentration, glucose concentration, excitatory amino acids concentration, lactate dehydrogenase concentration, hyaluronic acid concentration, uric acid concentration, calcium pyrophosphate concentration, beta-glucuronidase concentration, nerve growth factor concentration, insulin-like growth factor concentration, Caeruloplasmin concentration, and oxidase concentration.

21. The prosthetic device of claim 16, wherein the electronics structure includes a microcontroller and a transmitter.

22. The prosthetic device of claim 16, wherein the electronics structure includes an application specific integrated circuit, which includes a filter for filtering out low frequency noise.

23. The prosthetic device of claim 16, wherein the electronics structure includes an application specific integrated circuit, which includes an amplifier for amplifying signals from the sensor array.

24. The prosthetic device of claim 16, wherein the electronics structure includes an application specific integrated circuit, which includes a multiplexer for multiplexing signals from the sensor array.

25. The prosthetic device of claim 16, wherein the electronics structure includes an application specific integrated circuit, which includes an analog-to-digital converter for converting analog signals from the sensor array to digital signals.

26. The prosthetic device of claim 16, wherein the electronics structure includes an application specific integrated circuit, which includes a processor for processing signals from the sensor array.

27. The prosthetic device of claim 16, wherein at least one of the plurality of sensors comprises a microcantilever sensor detecting at least one of a predetermined component of the bodily fluid in the microchannel, a predetermined contaminant of the bodily fluid in the microchannel, and a predetermined property of the bodily fluid in the microchannel.

28. The prosthetic device of claim 27, wherein the microcantilever sensor comprises a first layer of a dual-layer structure and the electronics structure comprises a second layer of the dual-layer structure.

29. The prosthetic device of claim 27, wherein the microcantilever sensor comprises a reference cantilever exposed to a controlled environment devoid of biochemical agents and a sensing cantilever exposed to the bodily fluid and generating sensing signals, wherein vibration signals from the reference cantilever are operable to reduce interference in the sensing signals from the sensing cantilever caused by external vibrations.

* * * * *